(12) United States Patent
Glenn et al.

(10) Patent No.: US 6,190,303 B1  
(45) Date of Patent: Feb. 20, 2001

(54) SHIELD ASSEMBLY WITH REMOVABLE INNER-TUBE APPARATUS FOR RADIOACTIVE STENTS

(75) Inventors: Richard A. Glenn; Thomas H. Campbell, both of Redwood City; Todd H. Turnlund, Sunnyvale, all of CA (US)

(73) Assignee: IsoStent, Inc., Belmont, CA (US)

(*) Notice: Under 35 U.S.C. 154(b), the term of this patent shall be extended for 0 days.

(21) Appl. No.: 09/301,442

(22) Filed: Apr. 28, 1999

Related U.S. Application Data

(63) Continuation-in-part of application No. 09/236,770, filed on Jan. 25, 1999, now Pat. No. 6,132,358.

(51) Int. Cl.⁷ .................................................. A61N 5/00
(52) U.S. Cl. ................................................... 600/3; 600/1
(58) Field of Search ............................. 600/1, 3, 104, 600/107, 108

(56) References Cited

U.S. PATENT DOCUMENTS

| | | |
|---|---|---|
| 5,147,282 * | 9/1992 | Kan .......................................... 600/1 |
| 5,605,530 | 2/1997 | Fischell et al. . |
| 6,059,713 * | 5/2000 | Urick et al. .............................. 600/3 |

OTHER PUBLICATIONS

U.S. application Ser. No. 08/990,381, Fischell et al., filed Dec. 15, 1997.

* cited by examiner

*Primary Examiner*—Cary O'Connor  
*Assistant Examiner*—Navin Natnithithadha  
(74) *Attorney, Agent, or Firm*—Beyer Weaver & Thomas, LLP

(57) ABSTRACT

A radiation shield assembly (30) for a radioactive stent (11) mounted onto a deployment portion (20) of a delivery apparatus (12) including a relatively thin, elongated tube member (69) having a wall (70) defining a receiving passage (72) formed and dimensioned for axial receipt of the stent mounted onto the deployment portion therein to substantially prevent direct contact with the stent (11). A removal structure (71) cooperating with the wall (70) of the tube member (69) for longitudinal severing thereof to enable selective removal of the tube member from the delivery apparatus (12) for deployment use thereof.

71 Claims, 14 Drawing Sheets

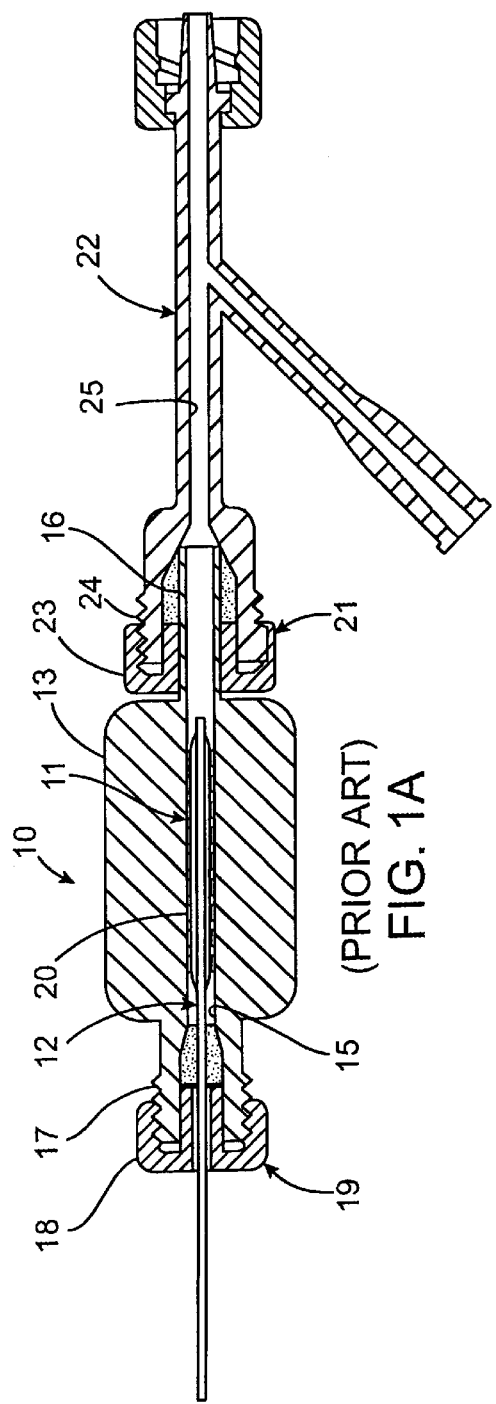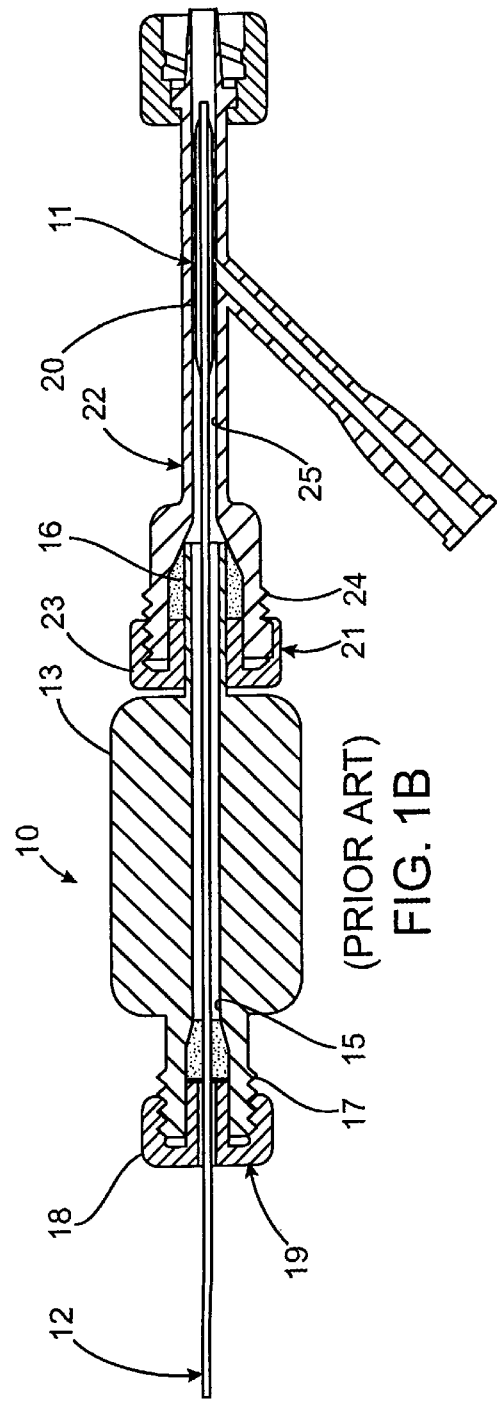

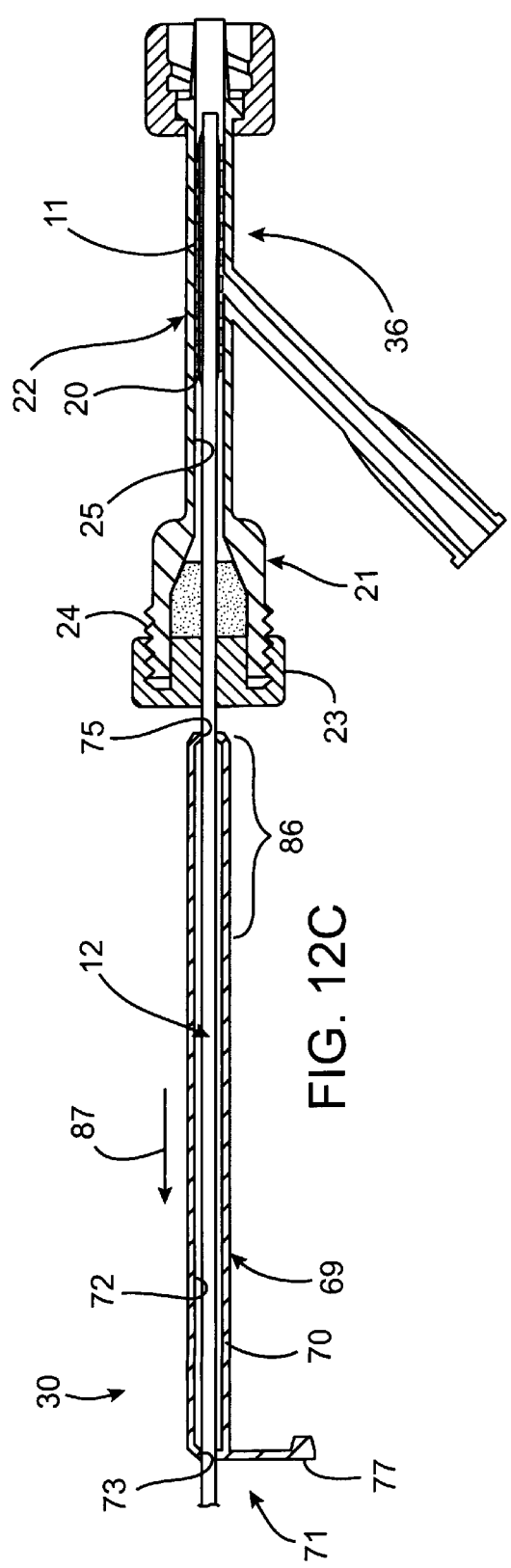
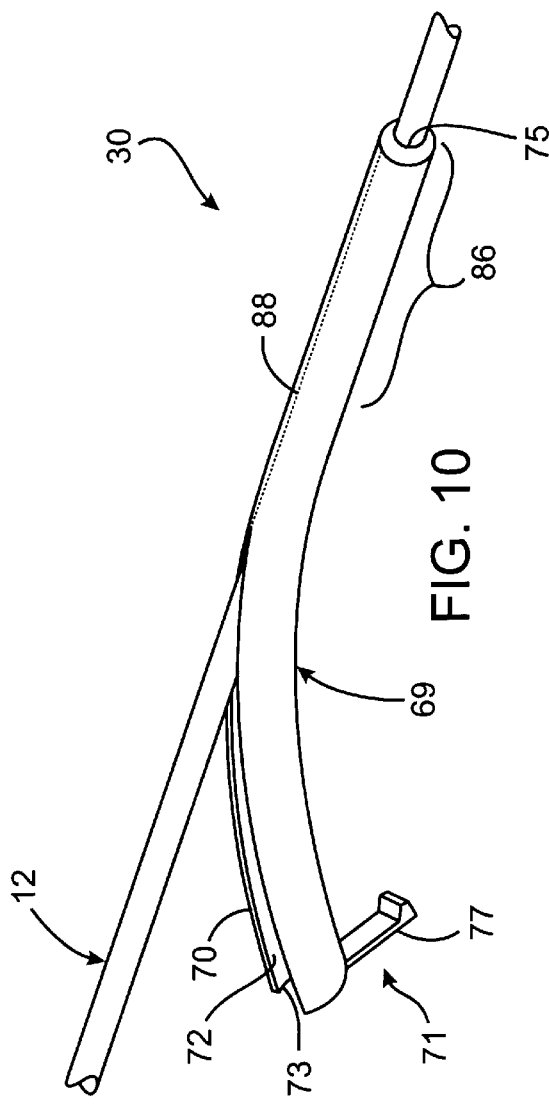

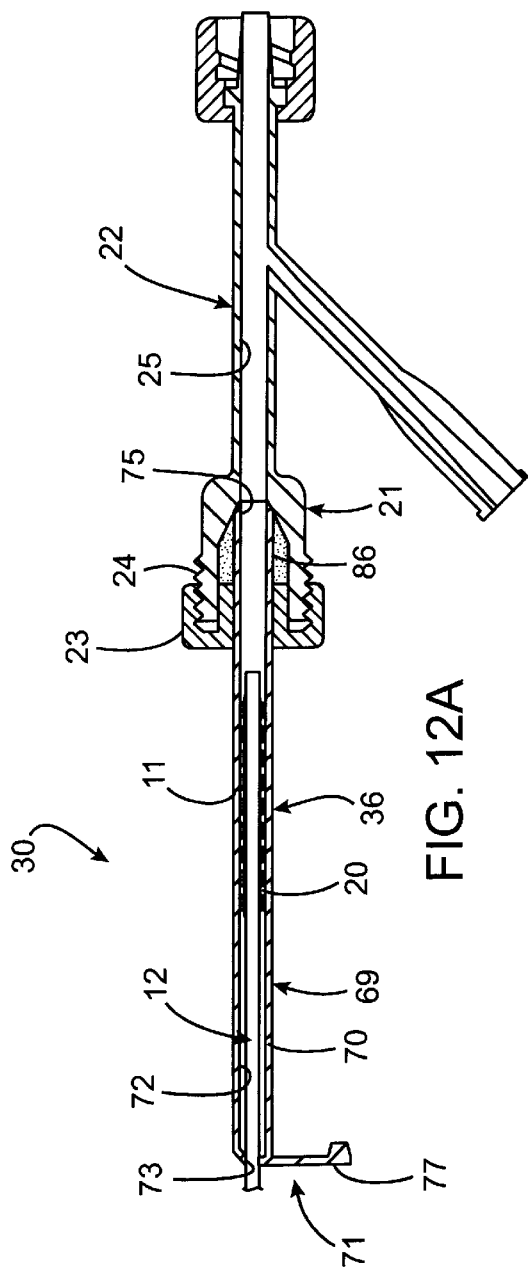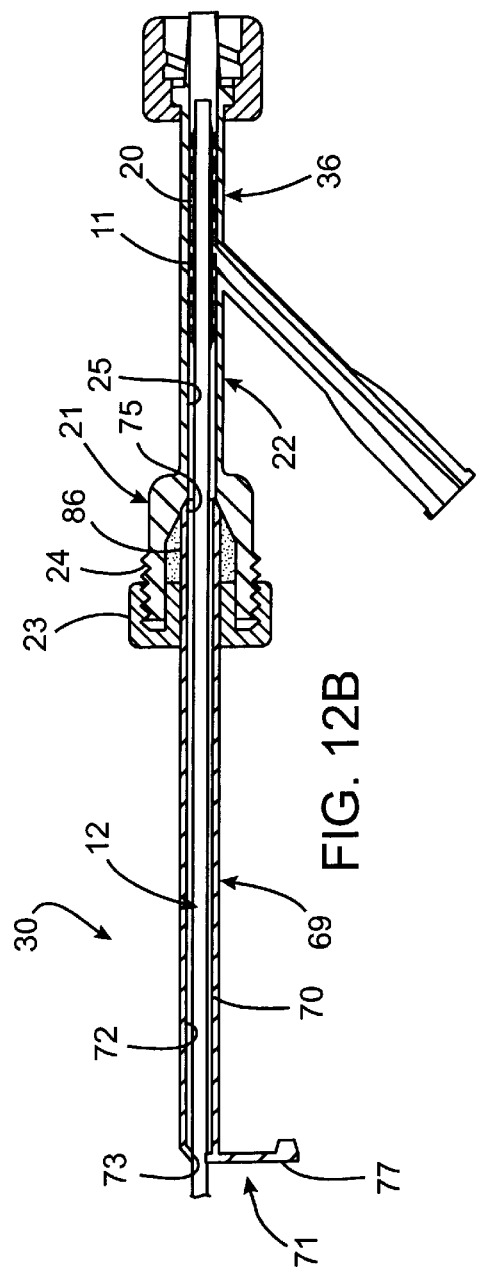
FIG. 12A
FIG. 12B

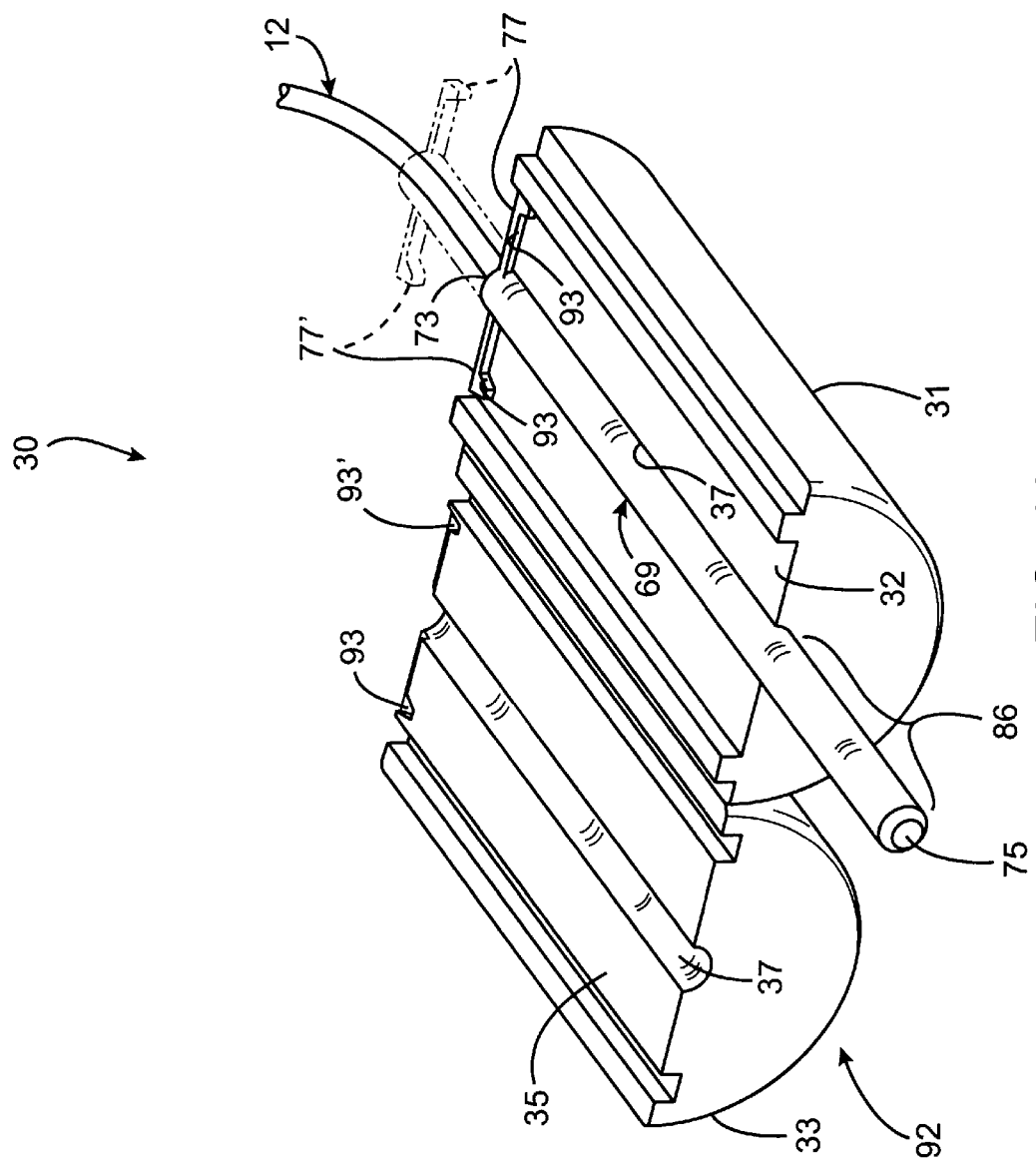

US 6,190,303 B1

SHIELD ASSEMBLY WITH REMOVABLE INNER-TUBE APPARATUS FOR RADIOACTIVE STENTS

RELATED APPLICATION

This application is a continuation-in-part application based upon U.S. patent application Ser. No. 09/236,770, filed Jan. 25, 1999, and entitled SHIELD ASSEMBLY FOR RADIOACTIVE STENTS now U.S. Pat. No. 6,132,358, issued Oct. 17, 2000.

TECHNICAL FIELD

The present invention relates, generally, to shield assemblies for radioactive devices and, more particularly, to radiation shields for radioactive stents and delivery catheters.

BACKGROUND OF THE INVENTION

Percutaneous Transluminal Angioplasty (PTA) is a medical procedure for widening a stenosis or constriction of a bodily passage. The most common application is to widen the passage of a blood vessel, such as an artery, which has been constricted by the build-up of cholesterol fats or atherosclerotic plaque. When this medical procedure is applied to a coronary artery, it is referred to as Percutaneous Transluminal Coronary Angioplasty (PTCA).

Typically, a tip mounted balloon of a balloon catheter is advanced over a guidewire to the stenosis. Once the balloon catheter is properly positioned, the balloon is inflated to compress the plaque against the vessel walls and widen the stenosis. Problems occur, however, when the dilatation of the occlusion forms fissures, flaps and/or dissections which may ultimately cause reclosure or restenosis of the vessel.

To maintain vessel patency and/or strengthen the area undergoing angioplasty or other treatment, an intravascular prosthesis may be employed. These devices are usually introduced percutaneously, transported transluminally and positioned at a desired location within the widened stenosis of the patient. One form of an intravascular prosthesis is a radially expandable stent device which is typically positioned at the tip of a balloon delivery catheter in a crimped condition. When the tip of the delivery catheter apparatus and the crimped stent are properly positioned at the desired location or the stenosis, the balloon is expanded to implant the stent in the widened vessel. In some instances, expansion of the balloon portion of the delivery catheter can simultaneously compress the plaque at that location and expand the stent to its proper implantation size. The balloon portion of the catheter is then deflated and withdrawn from the vessel, leaving the implanted radioactive stent as a permanent scaffold and as a deterrent to tissue growth in order to reduce the chance of restenosis.

More recently, these stents have been embedded or implanted with radioisotopes so that they emit predictable amounts of radiation into the widened vessel and immediate surrounding area. The nature of these radioactive devices is that regrowth of the tissue can be reduced by the radiation, and effect which is highly beneficial in preventing restenosis of the vessel.

Although these radioactive stents only emit relatively low levels of radiation, direct contact with the stent by physicians, laboratory technicians, and other personnel should be avoided. As a result, shielding devices 10 such as those shown in FIGS. 1A and 1B have been developed to enable the safe transportation and handling of radioactive stent 11 and/or a stent delivery catheter apparatus 12. Typical of these shields devices 10 is disclosed in U.S. Pat. No. 5,605,530 entitled "System for Safe Implantation of Radioisotope Stents" which is incorporated by reference in its entirety.

These radioactive shield devices 10 typically include one piece main body portions 13 having longitudinally extending central lumens 15 therethrough. Positioned in these lumens 15 in a retracted condition (FIG. 1A) are the stent delivery catheter apparatus 12 and crimped radioactive stent 11 for shielding thereof. Accordingly, this one-piece configuration enables safe transportation and handling of the radioactive stent before being inserted into the vessel.

The radiation shield device 10 further preferably includes a distal proboscis 16 and a proximal threaded section 17 which operates as a Tuohy-Borst fitting 19 onto which a nut 18 can be screwed. When the expandable balloon 20 of the delivery catheter and the distal mounted radioactive stent 11 are retracted in the central lumen 15 of the shield device 10 (FIG. 1A), a shield nut 18 may be tightened down on proximal threaded section 17, thereby frictionally coupling the stent delivery catheter apparatus 12 therein.

To insert the stent delivery catheter apparatus 12 and stent 11 into a vessel (not shown), the proboscis 16 of the shield device 10 is preferably inserted into another Tuohy-Borst fitting 21 of a guiding catheter. This union may be provided by a Y-adapter 22 having an adapter nut 23 tightened to the threaded end 24 to functionally couple and fluid seal the radiation shield device to the Y-adapter. Subsequently, the proximal shield nut 18 may be loosened to enable the mounted stent 11 and the delivery catheter apparatus 12 to be forwardly advanced (FIG. 1B) into a passage 25 of the Y-adapter 22 and into the vessel as a unit.

While this one-piece shield device is most adequate to shield personnel from radiation exposure from the radioactive stent, several problems are inherent in the design. For example, when the radiation shield device 10 is mounted to the Y-adapter 22, and the delivery catheter is slideably inserted through the central lumen 15 of the shield device and the passage 25 of the Y-adapter, the radiation shield device cannot be removed or separated from the delivery catheter apparatus 12 since the diameter of the central lumen is not sufficiently large to enable the proximal manipulating end of the catheter apparatus (not shown) to slide therethrough. Consequently, the depth of insertion of the delivery catheter is limited to the proximal end of the radiation shield device (i.e., the Tuohy-Borst fitting 19) rather than the proximal end of the Y-adapter 22 (i.e., the Tuohy-Borst fitting 21). Therefore, the useable length of the catheter 12 is decreased. Increasing the length of the catheter apparatus to compensate for the decrease of insertion depth may be problematic since any increase in length may incrementally reduce the ability to precisely control the stent placement. This configuration also limits the physicians choice of delivery catheters to only those provided with the stent.

Moreover, even should a length increase be unnecessary, manipulation of the catheter apparatus is still more difficult since the surgeon must now control the catheter from relatively cumbersome shield device as compared to the smaller proximal end of the Y-adapter. This is especially true in instances where the shield device 10 has been decoupled from the Y-adapter during stent deployment. The mere weight and bulkiness of the shield device 10 dangling from the catheter apparatus significantly reduces maneuverability and manipulation of the catheter. In fact, in some instances, care must be observed so that the weight of the shield device 10 does not retract the stent assembly from the vessel.

Another problem associated with this arrangement is that after the stent delivery catheter apparatus 12 and the mounted radioactive stent 11 have been passed through the central lumen 15 of the shield device 10 into the passage of the Y-adapter, it is difficult to reinsert the catheter apparatus and the stent back into the central lumen of the shield device 10, should this be necessary to abort the deployment procedure. Therefore, there is a need to enable removal of the radiation shield device from the delivery catheter apparatus during deployment of the stent.

SUMMARY OF THE INVENTION

To achieve the foregoing, the present invention relates to a shield assembly for a deformable stent mounted onto a deployment portion of a delivery apparatus. The shield assembly includes a relatively thin, elongated tube member having a wall defining a receiving passage formed and dimensioned for axial receipt of the stent mounted onto the deployment portion therein. This arrangement substantially prevents direct contact with the stent. The shield assembly further includes removal structure cooperating with the wall of the tube member for longitudinal severing thereof to enable selective removal of the tube member from the delivery apparatus for deployment use thereof.

In one embodiment, the tube member is deformable and adapted to be peeled away from the delivery apparatus upon severing of the wall. In another arrangement, the wall of a tube member may be sized for an interference fit with the mounted stent and the deployment portion of the delivery apparatus.

In another embodiment, the removal structure includes a tab member extending from and coupled to the tube member to enable gripping thereof for peeling-away of the tube member. The removal structure may include a longitudinally extending perforation to facilitate separation of the tube member from the stent during the severing motion.

A retaining mechanism may be included in another embodiment which is coupled to the tube member and adapted to selective prevent axial displacement between the deployment device and the tube member. This retaining mechanism is movable between an engaged condition, preventing axial displacement between the stent and deployment device contained in the tube member passage, and a disengaged condition, permitting axial displacement therebetween. Preferably, the retaining mechanism includes a pair of opposed engaging fingers configured to contact the delivery apparatus for frictional engagement therewith in the engaged condition. Each engaging finger may include a seal member configured to cooperate with one another to form a hemostatic seal with the delivery apparatus when positioned in the engaged condition to seal the proximal end of the passage.

In yet another configuration, the tube member includes a relatively rigid first tube section, and an opposed relatively rigid second tube section which together cooperate, in a closed condition, to define the receiving passage for receipt of the stent and the deployment portion therein. The removal structure includes a bonding material cooperating with the first and second tube sections to retain the tube member in the closed condition. The bonding material is further adapted to enable separation of the opposed first and second tube sections, to an opened condition, upon application of sufficient separation forces to overcome the bonding strength of the bonding material to sever the wall.

In still another embodiment, a radiation shield assembly is disclosed having an elongated tube member adapted to be removably disposed substantially around the collective longitudinal periphery of the stent and the deployment portion of the delivery apparatus. A radiation shield device is removably disposed peripherally about at least a portion of the elongated tube member such that the stent and the deployment portion are substantially contained within the shield device. This containment substantially prevents the passage of radioisotopes emitted from the stent radially out of the shield device.

The radiation shielding device, in one embodiment, includes a first shield member having a first mating surface, and a second shield member removably coupled to the first shield member. The second shield member includes an opposed second mating surface cooperating with the first mating surface to substantially radially enclose the tube member and contained stent therebetween. The first mating surface and the second mating surface further cooperate to define a channel therebetween, formed and dimensioned for longitudinal receipt of the tube member therein. The tube member may further form a distal proboscis portion for the shield assembly extending distally from the channel of the radiation shield when the stent is contained therein.

In another aspect, a method of storing a deformable stent mounted onto a deployment portion of a delivery apparatus is provided for transport and delivery of the stent. The method includes containing the stent and the deployment device into an axially extending receiving passage of a relatively thin, elongated tube member to substantially prevent direct contact with the stent. The method further includes providing removal structure cooperating with a wall of the tube member for longitudinal severing thereof to enable selective removal of the delivery apparatus from the tube member for deployment use thereof.

In yet another aspect of the present invention, a method is included for delivering a deformable radioactive stent mounted onto a deployment portion of a delivery apparatus. The method includes containing the stent and the deployment device in a passage of an elongated tube member to substantially prevent direct contact with the stent; and placing a proboscis portion of the tube member in communication with a fitting for receipt into the vessel. The next event includes axially advancing the mounted stent and the deployment device, relative the tube member, into the fitting; and removing the tube member from impeding contact with the delivery apparatus.

The removing the tube member includes longitudinal severing a wall of the tube member to enable the selective removal of the delivery apparatus from the tube member passage. This event further includes tearing-away the wall of the tube member to enable the selective removal of the delivery apparatus from the tube member passage. In one arrangement, the severing a wall includes pulling a tab member integrally formed in the wall of the tube member to enable severing of the tube member wall. The severing a wall event further includes severing the wall along a longitudinally extending perforation predisposed in the wall to facilitate separation of the delivery apparatus from the tube member during the severing motion.

In still another configuration of the present inventive method, the containing the stent and deployment device further includes containing at least a portion of the elongated tube member in a radiation shield device removably disposed peripherally about tube member such that the stent and the deployment portion are substantially contained within the shield device. This containment substantially prevents the passage of radioisotopes emitted from the stent radially out of the shield device. Therefore, in the preferred form, before the removing the tube member, removing the radiation shield device from contact with the delivery apparatus.

BRIEF DESCRIPTION OF THE DRAWINGS

The method and assembly of the present invention has other objects and features of advantage which will be more readily apparent from the following description of the Detailed Description of the Embodiments and the appended claims, when taken in conjunction with the accompanying drawing, in which:

FIGS. 1A and 1B are a sequence of cross-sectional side elevation views of a prior art one-piece radiation shield assembly coupled to a Y-adapter, and illustrating sliding movement of an enclosed delivery catheter and mounted radioactive stent from the shield assembly to the Y adapter.

FIG. 10 is a top perspective view of the removable tube member of FIG. 9 illustrating use of the removal structure to tear-away the tube member from the delivery catheter.

FIGS. 12A–12C are a sequence of cross-sectional side elevation views of the radiation shield assembly of FIG. 9 coupled to a Y-adapter, and illustrating separation of the tube member from the delivery catheter.

FIG. 16 is a top perspective view of radiation shield assembly of FIG. 9, including a two piece radiation shield device in an opened position to enable placement or removal of the tube member and radioactive stent to or from the shield device.

DETAILED DESCRIPTION OF THE EMBODIMENTS

Figure 2A:
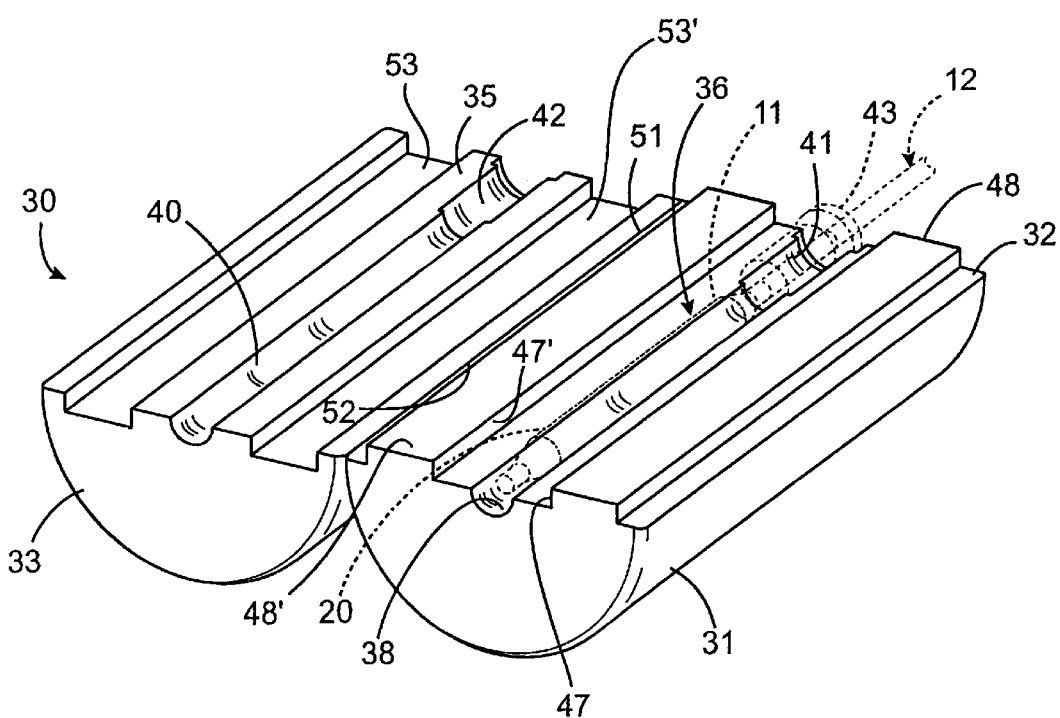
FIGS. 2A and 2B are a sequence of top perspective views of a first embodiment of a two piece radiation shield assembly constructed in accordance with the present invention, and illustrating movement between a closed position, enclosing at least the radioactive stent in a channel, and an opened position, enabling removal of the radioactive stent the shield assembly.

While the present invention will be described with reference to a few specific embodiments, the description is illustrative of the invention and is not to be construed as limiting the invention. Various modifications to the present invention to can be made to the preferred embodiments by those skilled in the art without departing from the true spirit and scope of the invention as defined by the appended claims. It will be noted here that for a better understanding, like components are designated by like reference numerals throughout the various figures.

Figure 2B:
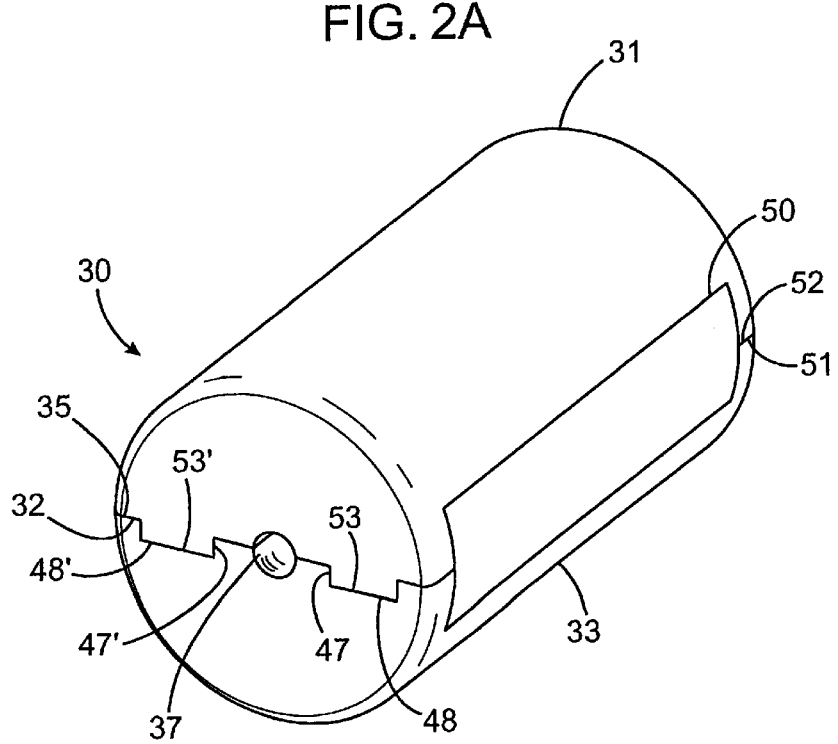

Referring now to FIGS. 2A and 2B, a radiation shield assembly, generally designated 30, is illustrated for shielding a radioactive stent 11 which is mounted to a distal portion of a stent delivery catheter apparatus 12 (both shown in dotted lines in FIG. 2A). The radiation shield assembly 30 includes a first shield member 31 having a first mating surface 32 and a second shield member 33 having an opposed second mating surface 35. The two shield members are removably coupled to one another, and the first mating surface 32 of the first shield member 31 and the second mating surface 35 of the second shield member 33 cooperate to substantially radially enclose the stent 11 therebetween in a manner substantially preventing the direct passage of radioisotopes emitted from the stent radially out of the shield assembly 30.

Accordingly, a two-piece radiation shield assembly 30 is provided which, in the "closed" position of FIG. 2B, functions to enclose both the distal portion of the stent delivery catheter apparatus and the mounted radioactive stent therein (hereinafter, the "stent assembly 36"). Thus, the radioactive stent maybe handled, transported and deployed without directly exposing personnel to the radiation emitted by the stent. However, the two shield members 31, 33 may be selectively oriented in an "open" position (FIG. 2A) which enables the shield assembly to be removed from the stent delivery catheter apparatus while the radioactive stent and distal portion of the catheter apparatus are being transvascularly maneuvered to the stenosis. Thus, the useable maneuvering length of the catheter apparatus is increased which increases depth insertion. Additionally, the ease of manipulating the position of the mounted stent 11 and expandable balloon 20 of the catheter apparatus 12 itself is augmented since the bulky radiation shield assembly will no longer impede movement. Moreover, in instances where the deployment procedure of the stent must be aborted, the stent assembly may be easily reinserted or retracted back into the shield assembly by fully or partially opening the two-piece shield.

Although the present invention is described herein in connection with radioactive stents and stent delivery catheters, it should be well understood to those skilled in the art that the present invention is not limited to these applications. For example, the shielding assembly of the present invention may be implemented in situations that require shielding of radioactive stents delivered from means other than stent delivery catheters, the delivery of other radioactive devices such as radioactive grafts, radioactive wires, radioactive coils, and radioactive balloon catheters or any combination thereof.

In the preferred embodiment, each shield member 31, 33 is semi-cylindrical in shape so that in the closed position a cylinder is formed. It will be appreciated, however, that other shapes are permissible as long as the structure provides adequate radiation shielding from the radioactive stent enclosed therein. To position the stent assembly 36 in the shield assembly 30, a channel 37 extends from one end of each shield member to an opposite end thereof which is formed and dimensioned for sliding receipt of the stent assembly therein. Moreover, to provide proper shielding from the radioisotopes emitted from the radioactive stent 11, the shield assembly in a closed position (FIG. 2A) must be of sufficient radial dimension or diameter to prevent passage of the particle therethrough. Thus, the necessary thickness of the shield assembly is a function of the shield material and the type of radioisotope emitted from stent. For example, when the shield members are formed from a moldable acrylic and the stent is embedded with a beta particle emitter such as Phosphorus 32 ($^{32}$P), or a beta and low energy gamma emitter such as Paladium 103 ($^{103}$Pd), the diameter of the shield assembly should be between about 1.0 inch to about 2.0 inches, and most preferably about 1.0 inches. Other suitable materials, of course, may be employed in whole or in part, such as a polycarbonate, acrylic/polycarbonate with a thin leaded outer shell or a high density metallic material or the like.

As best viewed in FIG. 2A, the length of each shield member 31, 33 is preferably slightly longer than the length of the distal portion of the catheter expandable balloon 20 and the mounted stent 11. This assures adequate shielding from the radioisotopes which are emitted from the radioactive stent 11 generally in directions radially from a longitudinal axis of the stent. Preferably, the length of the shield members extend about 1.0 cm to 2.0 cm past the proximal and distal ends of the stent.

In accordance with the present invention and as indicated above, the first shield member 31 includes a first mating surface 32, while the second shield member includes a second mating surface 35. When the shield assembly 30 is positioned in the closed position (FIG. 2B), the first and second mating surface 32, 35 are opposed one another, and are further configured to mate in a manner substantially radially enclose the stent 11 therebetween. Preferably, as shown in the first embodiment of FIGS. 2A and 2B, the first mating surface 32 of the first shield member 31 defines a longitudinally extending first channel portion 38, while the second mating surface 35 thereof forms a second channel portion 40.

These channel portions are preferably semi-cylindrical in shape and are positioned substantially co-axial with the shield assembly longitudinal axis. In the closed position, these channel portions cooperate to form channel 37 which is dimensioned for sliding and axial receipt of the stent assembly 36 therein.

At the proximal end of each channel portion 38, 40 is a semi-cylindrical bore portion 41, 42 having a diameter larger than that of the respective channel portion 38, 40. When oriented in the closed position, these bore portions 41, 42 collectively define a bore which is configured for receipt of an O-ring seal or first Tuohy-Borst fitting 43 (shown in broken lines) or the like therein. Thus, the stent assembly 36 may be releasably locked into the retracted position inside the shield assembly 30 upon tightening of the fitting 43.

Figure 3:
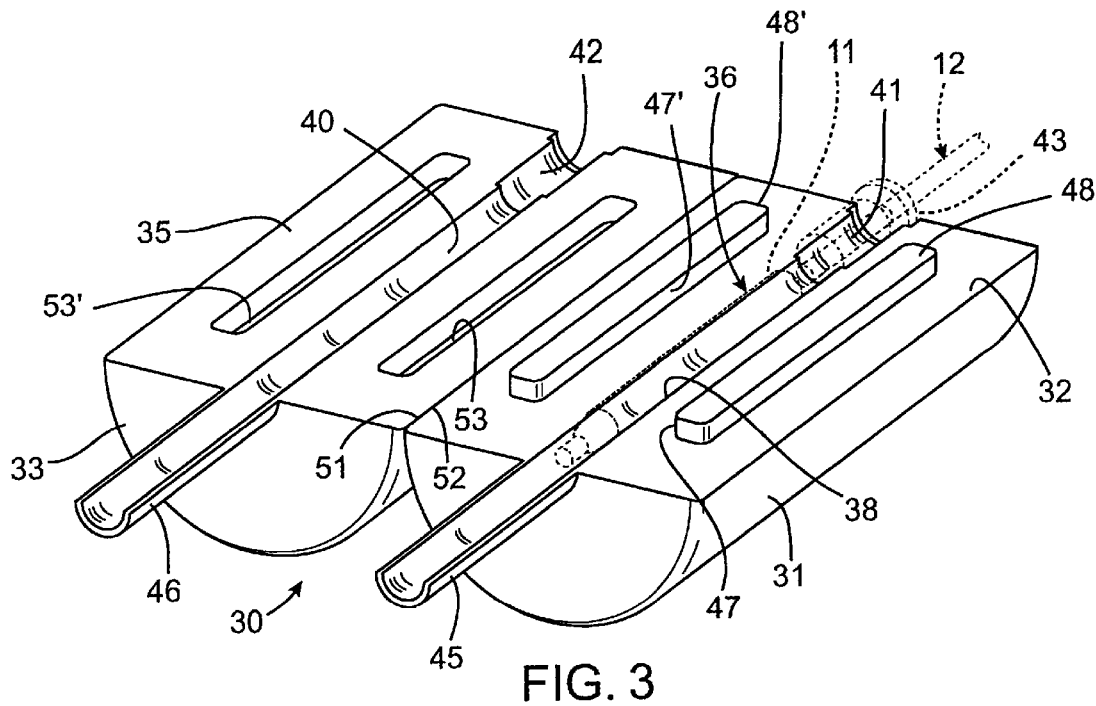
FIG. 3 is a top perspective view of a second embodiment of the present invention two piece radiation shield assembly in the opened position.

On the opposite distal end of the first and second shield members 31, 33 may be a first proboscis portion 45 and a second proboscis portion 46 (FIG. 3), respectively, which extend distally therefrom. In the closed position (not shown), these proboscis portions 45, 46 collectively form a proboscis which is preferably dimensioned thereof for receipt in a second Tuohy-Borst fitting or the like (not shown). Similar to the prior art embodiment of FIGS. 1A and 1B, the first and second Tuohy-Borst fittings may be adjusted so that the stent assembly 36 may be advanced through a Y adapter and into a vessel for deployment of the stent. It will further be appreciated that while only the embodiment of FIG. 3 illustrates the addition of a proboscis, any of the embodiments of the present invention may also include one.

In accordance with the present invention, the first and second mating surface 32, 35 cooperate to substantially prevent the passage of radioisotopes between the opposed shield member 31, 33, when in the closed position. As the radioisotopes are emitted from the stent, they travel along relatively linear paths, and away from the stent outer surface in directions generally radially away from the longitudinal axis of the stent. Thus, some of these radioisotopes will initially pass through the gap formed between the first mating surface 32 of the first shield member 31 and the second mating surface 35 of the second shield member 33 both of which internally terminate at the channel 37. On an atomic level this gap formed between the first mating surface 32 and the second mating surface 35 may be relatively large in some regions. Accordingly, the first and second mating surfaces are configured to eliminate any direct linear paths which extend from the channel 37 to an exterior portion of the shield assembly 30.

Figure 4:
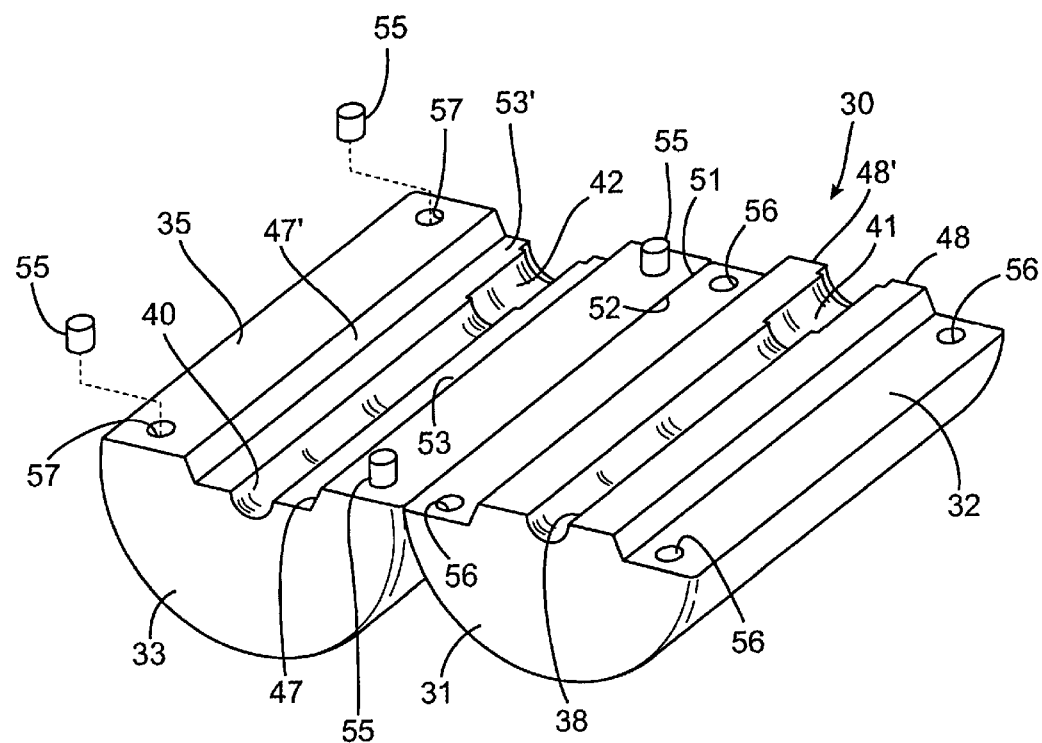
FIG. 4 is a top perspective view of a two piece radiation shield in the opened position in accordance with a third embodiment of the invention.
Figure 7:
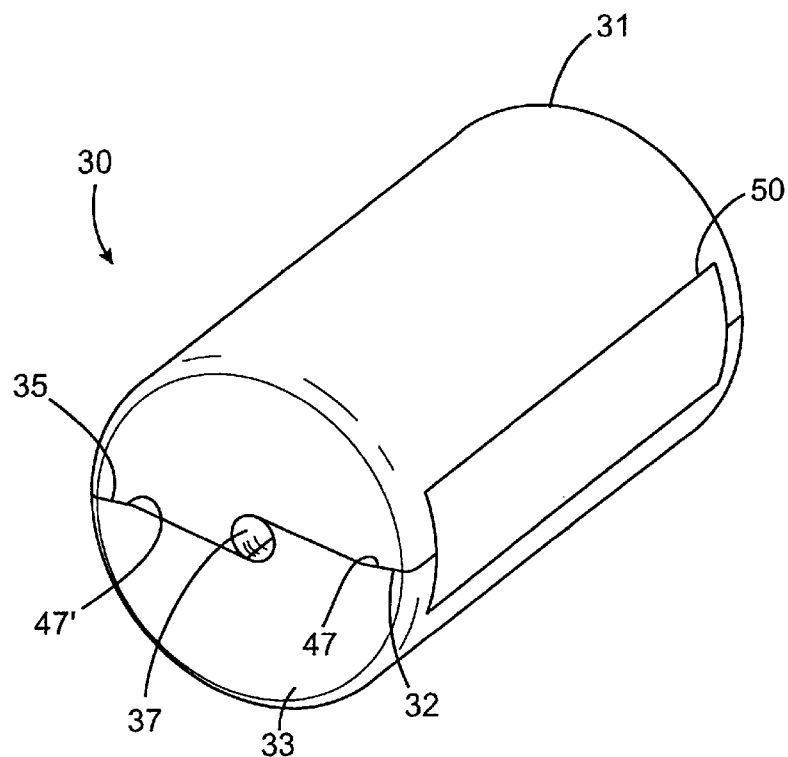
FIG. 7 is a top perspective view of a two piece radiation shield in the closed position in accordance with a sixth embodiment of the invention.
Figure 8:
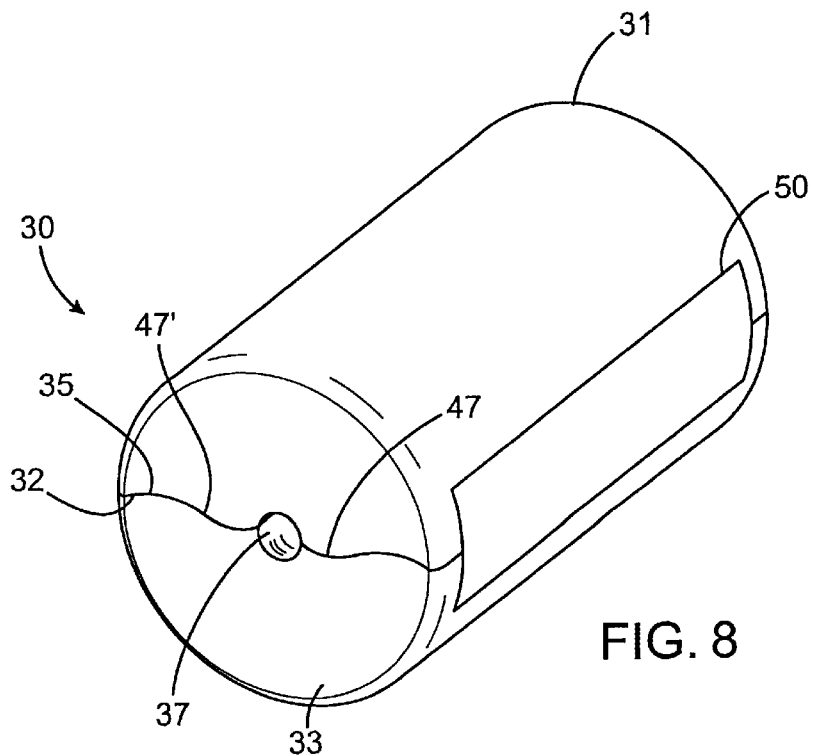
FIG. 8 is a top perspective view of a two piece radiation shield in the closed position in accordance with a seventh embodiment of the invention.

Referring back to FIGS. 2A and 2B, for example, the opposed first and second mating surface 32, 35 may be substantially planar for the most part to ease manufacture. However, at some position therealong, the respective surface 32, 35 will be sufficiently skewed relative these planes containing the surfaces such that radioisotopes emitted from the stent which are travelling between and in a direction relatively parallel to these opposed planes will contact this skewed surface. Therefore, at least one of the first mating surface 32 and the second mating surface 35 includes a side wall portion 47, 47' which is sufficiently skewed relative the plane to prevent passage of these linearly traveling radioisotopes through surface gap and out of the shield assembly 30. These side wall portions 47, 47' need not be perpendicular to the respective plane, but may be tapered, as shown in the embodiment of FIG. 4, or may be relatively gradually sloped, as viewed in the embodiment of FIG. 7. Moreover, the side wall portions 47, 47 may even be curvilinear (FIG. 8), as long as an isotope passing linearly between the opposed first and second mating surfaces would eventually impact one of these side wall portions thereof. Essentially, in any linear direction, an isotope will be physically stopped by a consistent solid material having a sufficient thickness specific to the isotope (E.g., about 0.29 in. acrylic for Phosphorus 32 ($^{32}$P)).

In the preferred embodiment, each side wall portion 47, 47' extends substantially longitudinally along the respective shield member 31, 33 from a proximal end to a distal end thereof. Further, these walls extend substantially parallel to the longitudinal axis of the channel 37, although it will be understood that they may be relatively skewed as well. As viewed in the embodiment of FIG. 3, the side wall portions 47, 47' may only extend partially along the respective channel portions 38, 40. In this arrangement, the length of the side wall portions 47, 47' are preferably at least substantially equal to the length of the radioactive stent 11 mounted to the delivery catheter apparatus 12. Moreover, to assure containment of the radioisotopes, the side portions preferably extend longitudinally along the channel at positions substantially adjacent the stent 11 when in the stent assembly 36 is in the retracted position. FIG. 3 best illustrates this concept by providing first and second alignment prongs 48, 48' (to be discussed below in greater detail) at an orientation adjacent to the stent 11. These prongs include side wall portions sufficiently long and properly oriented to substantially prevent the radioisotopes from passing through the gap and out of the shield assembly.

A coupling device, generally designated 50, preferably couples the second shield member 33 to the first shield member 31 for movement between the opened position (FIG. 2A) and the closed position (FIG. 2B). In one embodiment, the coupling device may be provided by a hinge member 50 or the like movably mounting one edge 51 of the first mating surface 32 to an opposed edge 52 of the second mating surface. Thus, the first shield member 31 is pivotally mounted to the second shield member between the opened and closed position, and about a longitudinal axis positioned at the opposed edges 51, 52 of the shield members. For example, the hinge member may be a mechanical door-type hinge or simply a strip of adhesive tape 50. As another example, the coupling device may be provided by a perforated shrink wrap material shrunk around the two halves retaining them in an aligned form. When removal of the shield assembly from the catheter is necessary, the shrink wrap may be torn or removed from the shield assembly so that the shield members may be separated.

On the opposite side of each shield member 31, 33, mating latch members (not shown) may be provided which releasably latch the shield members together in the closed position. Upon unlocking of the latch members, the shield assembly may be pivotally moved to the opened position so that the stent assembly or catheter assembly can be removed. These latch members may be provided by any conventional latch devices employed in the field.

To facilitate alignment between the first shield member 31 and the second shield member so that the respective channel portions 38, 40 align for receipt of the stent assembly 36 in the closed position, the shield assembly 30 preferably includes an alignment device therebetween. In one embodiment, the alignment device may be provided by a longitudinally extending first alignment prong 48 (FIGS. 2, 3 and 5) upstanding from the first mating surface, and positioned on one side of the first channel portion 38. This first alignment prong 48 preferably extends from proximate one end of the first channel portion 38 to proximate an opposite end thereof, and is preferably oriented substantially parallel to the channel portion. More preferably, the prong extends completely from the proximal end of the shield assembly to the distal end thereof.

The second mating surface 35 of the second shield member 33 provides a first recess 53 formed and dimensioned for sliding receipt of the first alignment prong 48 therein. Such receipt is preferably relatively tight so as to properly align the first and second channel portions 38, 40 when the first and second shield members are mounted together in the closed position. However, the tolerance must not be so small as to substantially impede or prevent movement of the shield assembly 30 between the closed position and the opened position.

In a similar manner, on the opposite side of the respective channel portions 38, 40, the first mating surface 32 and the second mating surface 35 preferably define a second alignment prong 48' and a corresponding second recess 53'. In the closed position, the first and second alignment prongs 48, 48' are slideably received in the respective first and second recesses 53, 53' for alignment of the first shield member 31 with the second shield member 33. Similar to the first alignment prong 48, the second alignment prong 48' upstands from the first mating surface 32 of the first shield member 31, and preferably longitudinally extends from the proximal end of the shield assembly to the distal end thereof. As shown in the embodiment of FIG. 3, however, the alignment prongs 48, 48' and corresponding recesses 53, 53' may only extend from proximate one end of the respective channel portion 38, 40 to an opposite end thereof.

The side walls defining the height of the first and second prongs 48, 48' may upstand substantially perpendicular from the first mating surface 32, as shown in FIGS. 2A and 2B. Alternatively, in the embodiment of FIG. 3, these side walls may be tapered inwardly to facilitate opening and closing of the shield assembly, In this configuration, the opposed side walls defining the corresponding recesses 53, 53' would be similarly tapered for mating therebetween. Moreover, it will be appreciated that these prongs and corresponding recesses may be interchanged on the mating surfaces without departing from the true spirit and nature of the present invention.

Turning now to FIGS. 4 and 5, the present invention may include dowel pins 55 or the like as an alignment device. Thus, to properly align the first and second shield members 31, 33 in the closed position, at least two dowel pins 55 are employed on opposite sides of the channel portions 38, 40. Preferably, however, four dowel pins 55 are strategically positioned at or proximate to the four corners of the first and second mating surface 32, 35. Corresponding dowel bores 56 and 57 are formed into the mating surface 32, 35 and are configured for sliding receipt of a respective dowel pin 55 therein. Therefore, the dowel bores 56 of the first mating surface 32 must be co-axially aligned with the dowel bores 57 of the second mating surface 35 for align receipt of the dowel pin.

The dowel pins may be more permanently anchored to one of the first shield member 31 or the second shield member 33, or a combination thereof. This assures that the dowel pin will not inadvertently dislodge from the corresponding dowel bores 56, 57 during separation from of the shield members the closed position to the opened position. Moreover, these dowel pins 55 may be adapted to provide a snap-type fit with the corresponding dowel bore for additional securing purposes. In this arrangement, these alignment dowel pins may further function as the coupling device and/or as a latch device between the two shield members. This may be especially true of the configuration of FIG. 4 where alignment prongs 48, 48' are already provided.

In accordance with the present invention, the alignment prongs 48, 48 and corresponding recesses 53, 53' may also integrally provide the side wall portions 47, 47' extending longitudinally along the channel 37. Thus, either the side walls of the prongs 48, 48' or the side walls of the recesses 53, 53' form the side wall portions 47, 47 necessary to impede passage of the radioisotopes out of the shield assembly. Accordingly, the alignment prongs 48, 48', such as those shown in FIG. 3, must be sufficiently thick to shield radiation exposure. As mentioned above, this calculation is in part dependent upon the prong composition and the intensity of the radioisotope embedded in the stent 11.

Figure 5A:
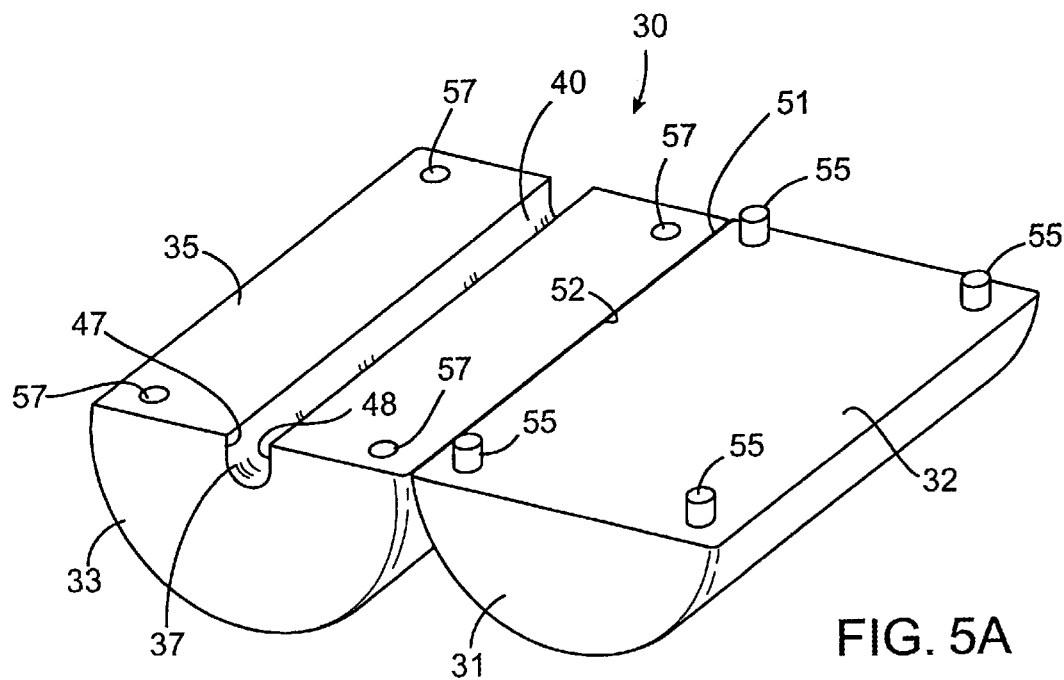
FIGS. 5A and 5B are a sequence of top perspective views of a fourth embodiment of the present invention illustrating movement between the closed position and the opened position.

Referring now to FIGS. 5A, an alternative embodiment of the present invention is provided wherein the first mating surface 32 of the first shield member 31 is substantially planar, while the second mating surface 35 of the second shield member 33 primarily defines the channel 37. In this embodiment, the stent assembly (not shown) is located in the U-shaped second channel portion 40 at a position sufficiently below the gap formed between the first mating surface 32 and the second mating surface 35 in the closed position. The radioisotopes emitted substantially linearly from the stent surface, accordingly, cannot not enter the gap in a direction substantially parallel thereto. This embodiment, thus, substantially contains the radioisotopes within the shield assembly 30 since these particles entering the gap will eventually impact the first mating surface 32 of the first shield member 31.

Figure 5B:
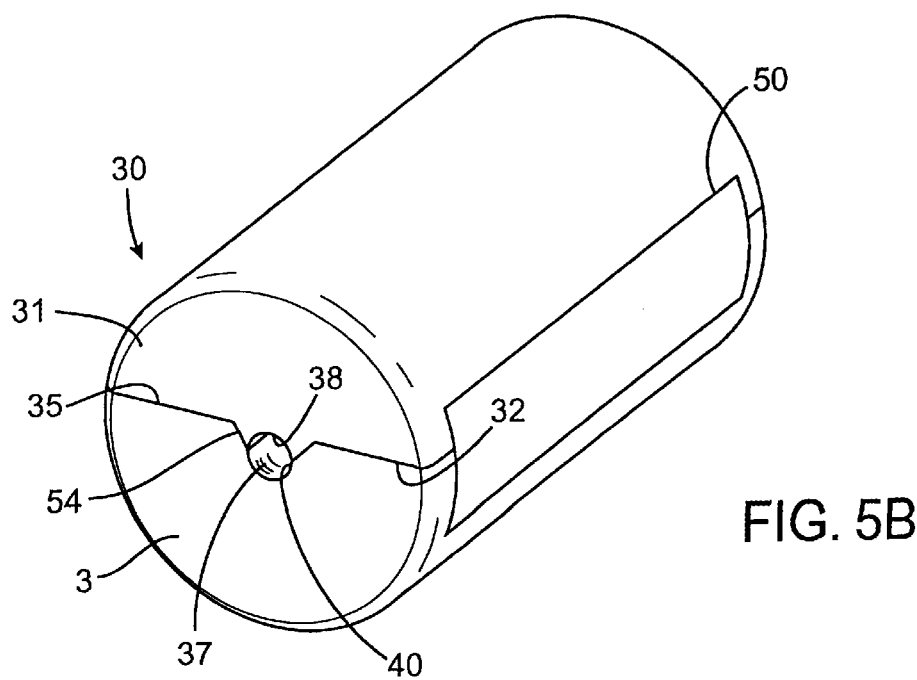

Similarly, in the embodiment of FIG. 5B, a pair of off-set first and second shield members 31, 33 are provided having substantially planar respective first and second mating surfaces 32, 35. In this embodiment, however, the first mating surface 32 provides a longitudinally extending protrusion portion 54 forming a semi-cylindrical first channel portion 38. This protrusion portion 54 has tapered outer walls formed to extend into the opposed U-shaped second channel portion 40 in an aligned manner such that in the closed position, the protrusion portion 54 cooperates with the U-shaped channel portion 40 to enclose a stent therein. Unlike the previous embodiment, a substantially cylindrical channel 37 is formed.

Figure 6A:
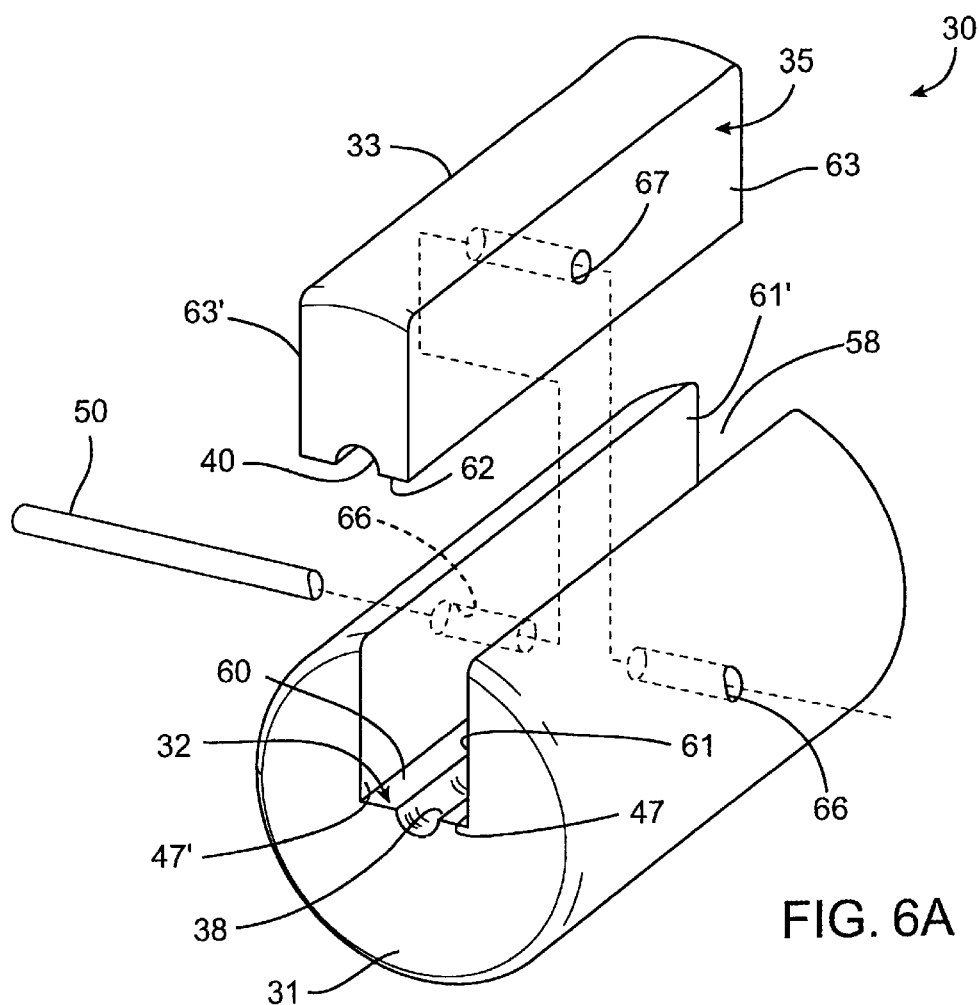
FIGS. 6A and 6B are a sequence of top perspective views of a fifth embodiment of the present invention illustrating movement between the closed position and the opened position.
Figure 6B:
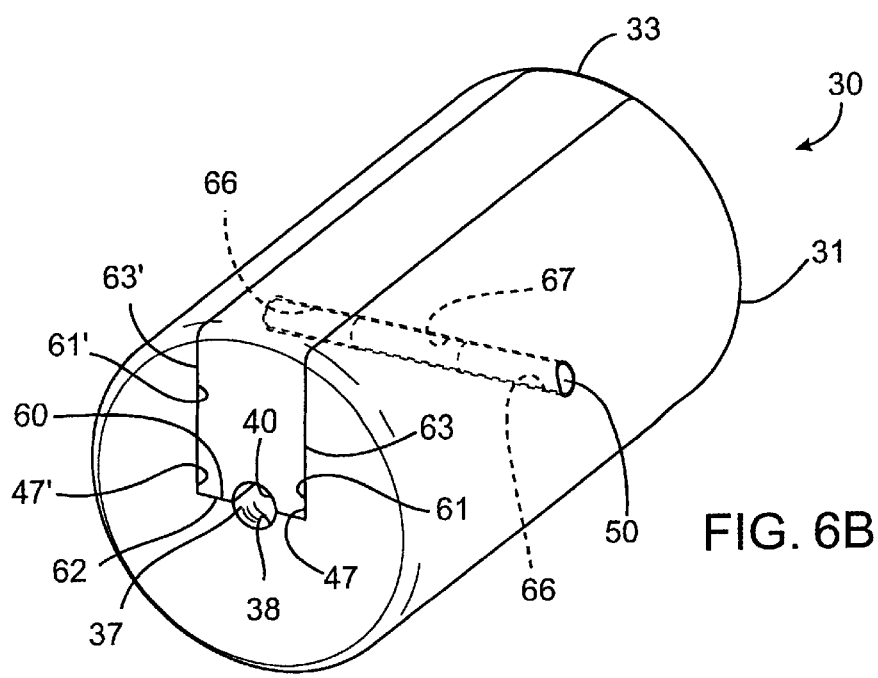

In the embodiment of FIGS. 6A and 6B, a radiation shield assembly 30 is provided wherein the first mating surface 32 of the first shield member 31 defines a longitudinally extending receiving slot 58 formed and dimensioned for sliding receipt of a key-shaped second shield member 33 between the opened position (FIG. 6A) and the closed position (FIG. 6B). According to the present invention, the first mating surface 32 of the first shield member 31 and the second mating surface 35 of the second shield member 33 cooperate to substantially radially enclose the stent 11 therebetween in a manner substantially preventing the direct passage of radioisotopes emitted from the stent radially out of the shield assembly 30.

The first mating surface 32 further includes a first support wall 60 defining the first channel portion 38. On each side of the first support wall 60 is a first alignment wall 61 and an opposite second alignment wall 61', each of which is disposed at an angle skewed relative to the first support wall 60. As shown in FIGS. 6A and 6B, the first and second alignment walls 61, 61' are preferably substantially perpendicular to first support wall 60. However, this skewed angle may be oblique or obtuse as well. Collectively, the first support wall 60, the first alignment wall 61 and the second alignment wall form the receiving slot 58.

The second mating surface of the second shield member 33 provides a second support wall 62 defining a second channel portion 40. Hence, in the closed position (FIG. 6B), the first and second channel portions 38, 40 cooperate to define the channel 37 formed for receipt of the stent assembly 36. It will be understood, however, that the configuration of FIGS. 5A and 5B may be employed as well.

Similar to the first shield member 31, on each side of the second support wall 62 is a first contact wall 63 and an opposite second contact wall 63', each of which is disposed at an angle skewed relative to the second support wall 62.

The skewed angle of the contact walls 63, 63' relative the second support wall 62, of course, must be substantially equal to that between the opposed alignment walls 61, 61' and the first support wall 60. Accordingly, the second shield member 33 is formed and dimensioned for sliding receipt in the receiving slot 58 of the first shield member 31 between the opened and closed position. Moreover, the spacing of the As shown in FIGS. 6A and 6B, the first and second alignment walls 61, 61' are preferably substantially perpendicular to first support wall 60. However, this skewed angle may be oblique or obtuse as well.

The first support wall 60, and the first and second alignment walls 61, 61' of the first shield member 31 all extend longitudinally from the proximal end of shield assembly 30 to the opposite distal end thereof, while the second support wall 62, and the first and second contact walls 63, 63' of the second shield member 33 all extend longitudinally from the proximal end to the opposite distal end of the shield assembly. As illustrated in FIG. 6B, when the first alignment wall 61 and the second alignment wall 61 respectively engage the first contact wall 63 and the second contact wall 63', and the first support wall 60 engages the second support wall 62, the first shield member 31 slideably couples together with the second shield member 33 toward the closed position. When properly aligned, the first channel portion 38 and the second channel portion 40 cooperate to form channel 37 to which slideably receives stent assembly (not shown) therein. As previously indicated, this cooperation between the first mating surface and the second mating surface substantially prevents the direct passage of radioisotopes emitted from the stent radially out of radiation shield assembly 30.

While this embodiment illustrates the skewed walls at about 90°, it will be understood that any other angles may be employed which are sufficient to prevent the passage of the linearly directed isotopes emitted from the channel 37.

A coupling device 50 is provided to couple the second shield member 33 to the first shield member when oriented in the closed position. As best viewed in FIG. 6A, the coupling device is preferably provided by a pin member 50 that is removably positioned in and extending through first shield member 31 and second shield member 33 when the two are mounted together in a closed position. To position the pin member 50 through the first shield member, a first passage 66 extends laterally therethrough and across the receiving slot 58. The diameter of the first passage is substantially similar to that of the pin member to enable sliding receipt therein. The coupling device 50 further includes second passage 67 extending laterally through the second shield member 33 and having a diametric dimension substantially similar to that of the first passage 66. Other coupling devices may be employed as well such as the above-mentioned shrink wrap materials enveloping the shield assembly.

It will be understood that second passage 67 of the second shield member 33 will be oriented and positioned substantially in co-axial alignment with the first passage 66 when the shield assembly is in the closed position. Subsequently, the pin member 50 may be slideably inserted through the first and second passages. Thus, the pin member may also function to align and latch the two shield members together as well.

Figure 9:
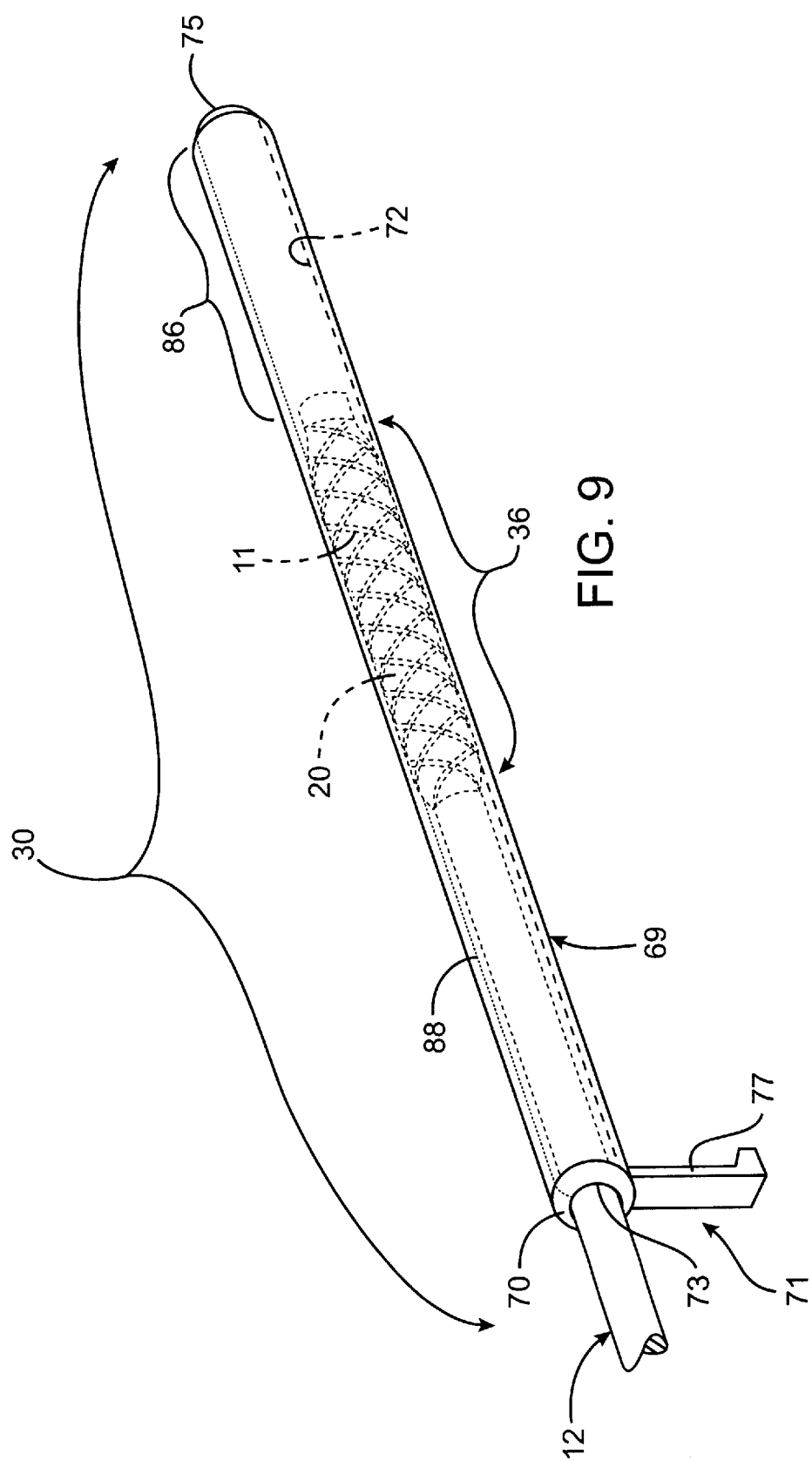
FIG. 9 is a top perspective view of an alternative radiation shield assembly having a removable tube member designed in accordance with the present invention.

Turning now to FIGS. 9 and 10, an alternative shield assembly 30 embodiment of the present invention is provided wherein a relatively thin, elongated tube member, generally designated 69, includes a wall 70 defining a receiving passage 72 formed and dimensioned for axial receipt of the stent mounted 11 onto the deployment portion 20 of the delivery apparatus 12 therein to substantially prevent direct contact with the stent 11. The shield assembly 30 further includes removal structure, generally designated 71, adapted to enable selective removal of the tube member 69 from the deformable stent 11 and delivery apparatus 12 for deployment use thereof (FIG. 10).

Accordingly, the tube member provides a thin, elongated peripheral cover which substantially prevents inadvertent contact with the stent mounted on the deployment portion of the delivery apparatus, while further providing a degree of radiation shielding when radioisotope stents are being utilized. When the mounted stent and the delivery apparatus are ready for delivery application, the protective tube member may be easily removed from the delivery apparatus for unencumbered manipulation thereof with respect to the radiation shield assembly.

Briefly, the mounted stent 11 and the deployment portion 20 of the delivery apparatus are again referred to as the "stent assembly 36." Furthermore, the delivery apparatus 12 is preferably provided by a delivery catheter, while the deployment portion 20 is preferably provided by an expandable balloon disposed at a distal portion of the delivery catheter. Other conventional delivery apparatuses and associated deployment devices may be employed, however. Finally, while this configuration of the present invention is generally described in connection with radioactive stents, it will be understood that this concept may be applied to nonadioactive radioactive stents as well without departing from the true spirit and nature of the present invention.

In the preferred form of this embodiment of the present invention and as shown in broken lines in FIG. 9, the tube member 69 is dimensioned to extend substantially peripherally around and distally past the stent assembly 36. The longitudinal length of the tube member 69 is therefore preferably at least slightly longer than the stent assembly 36 to assure full protective coverage of the mounted stent thereon.

The receiving passage 72 extends longitudinally from the proximal end to a distal end thereof which is formed for selective retainment of the stent assembly 36 therein during transport and storage. The receiving passage 72 is further dimensioned to enable sliding axial displacement between the stent assembly 36 and the tube member 69 when the stent assembly 36 is being prepared for advancement into the vessel. Accordingly, by way of example, for a stent assembly having a diameter on the order of about 0.067 inch to about 0.089 inch, the diameter of the receiving passage may be on the order of about 0.072 inch to about 0.094 wherein the tolerance therebetween is in the range of at least about 0.005 inch.

In the preferred form, the tube member is preferably substantially continuous having a proximal opening 73 and a distal opening 75 into the receiving passage 72. When the stent assembly 36 is contained within the tube member 69 for storage and/or transport, the distal opening 75 which extends distally past the delivery assembly may be closed-off to substantially reduce or eliminate the entrance of contaminates into the tube member passage 72. This may be performed by adding an additional shrink wrap material or the like over the distal section of the tube member, or by obstructing the distal opening with a removable plug, neither of which is illustrated.

While relative axial displacement between the tube member 69 and the stent assembly 36 is necessary to position and deploy the stent in the vessel, such relative movement may be detrimental during storage and/or transport thereof. Inadvertent relative displacement may not only expose personnel to radioistopes emitted from a radioactive stent, but may also expose the stent to contaminants which may render it unuseable.

Figure 11A:
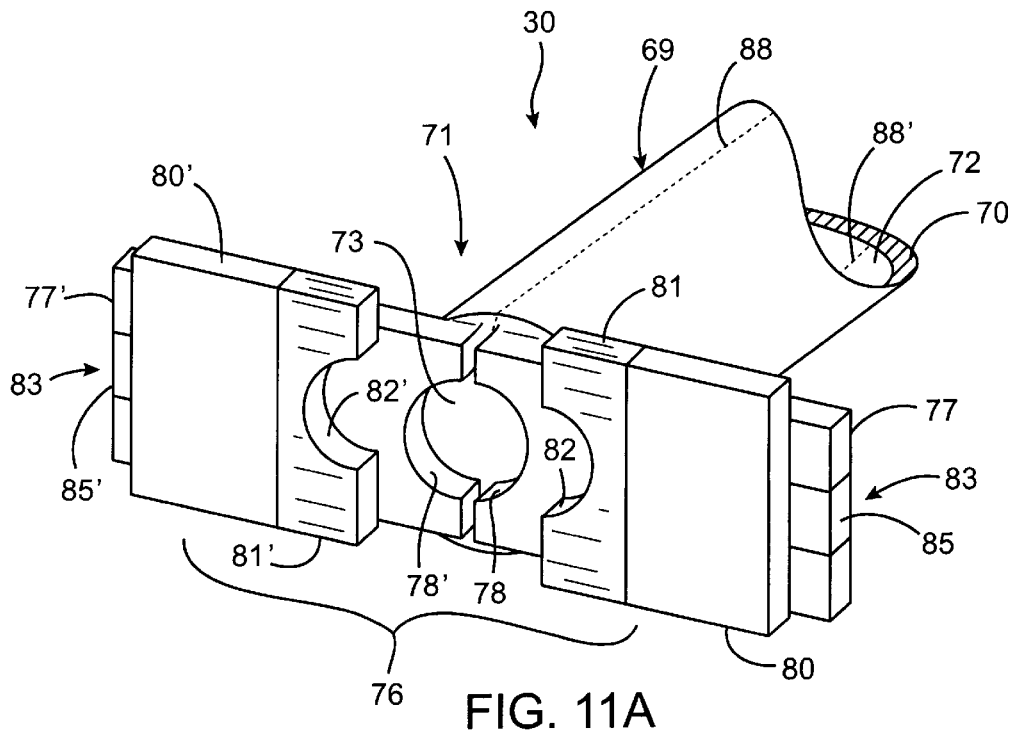
FIGS. 11A–11C are a sequence of enlarged, fragmentary top perspective views of a retaining mechanism mounted to the tube member, and illustrating engaging and disengaging movement with the delivery catheter.
Figure 11B:
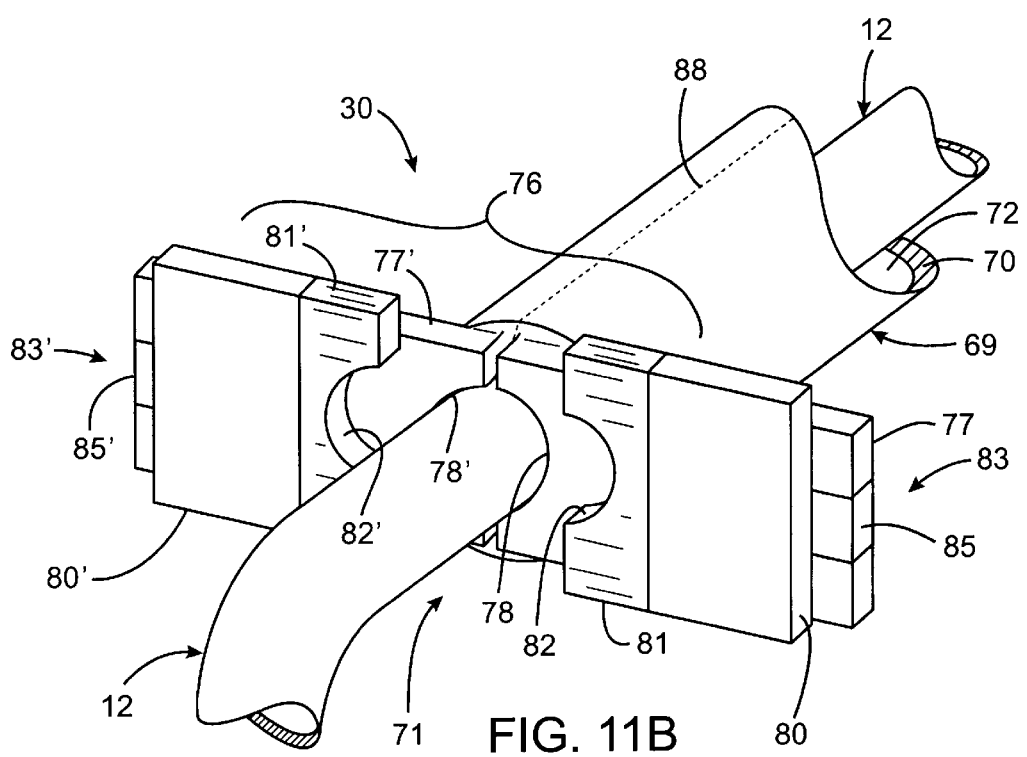
Figure 11C:
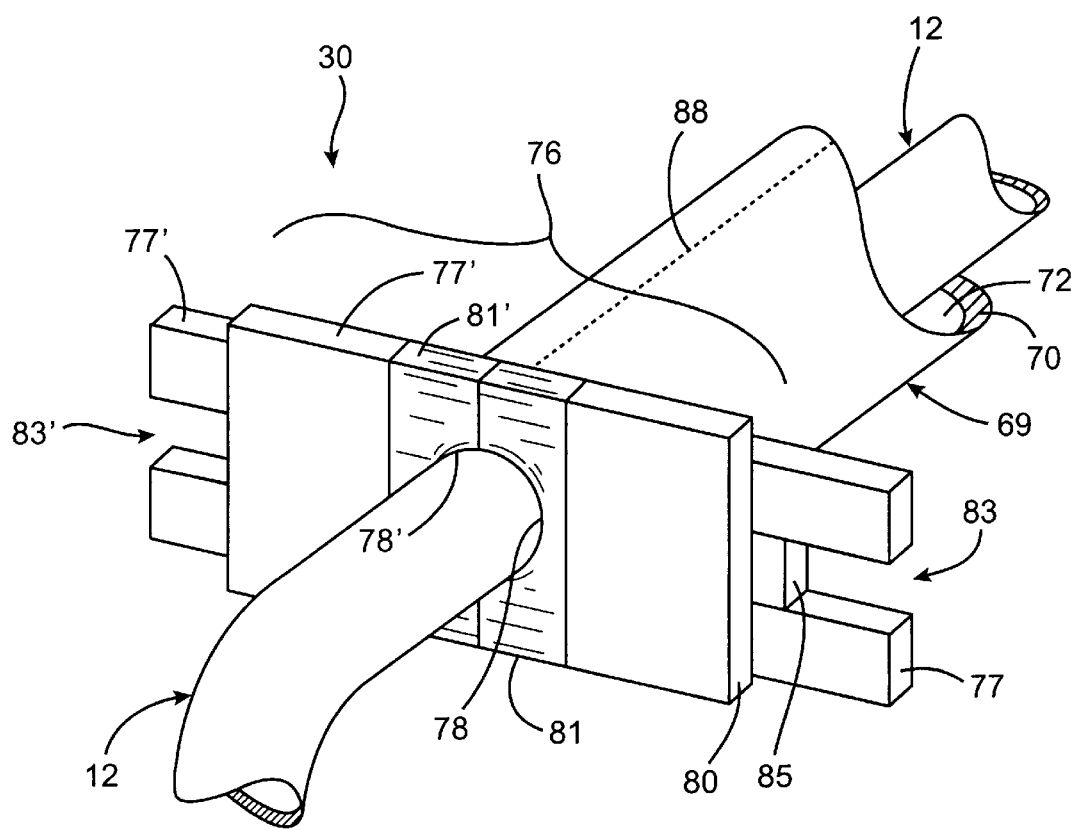

Accordingly, a retaining mechanism 76 is preferably provided which selectively prevents relative movement between the stent assembly 36 and the tube member 69 for containment therein. As best shown in FIGS. 11A–11C, the retaining mechanism 76 is movable between an engaged condition (FIG. 11C), preventing relative displacement between the tube member 69 and the stent assembly 36, and a released condition (FIG. 11B), enabling sliding axial displacement therebetween.

This retaining mechanism 76 is preferably incorporated into the opposed tab members 77, 77' of the removal structure 71. These tab members, which will be discussed in greater detail below, provide a means for gripping or the tube member to facilitate severing thereof. Each tab member 77, 77' is generally rectangular-shaped having a lower surface fixedly attached or integrally mounted to the proximal end of the tube member 69. Accordingly, when the tab members 77, 77' are manually separated, they will forcibly sever the tube member 69 to enable removal of the delivery catheter apparatus 12 from the tube receiving passage 72.

The tab members 77, 77' are preferably oriented substantially perpendicular to the longitudinal axis of the tube member such that they collectively extend substantially over the proximal opening 73 of the receiving passage 72. FIG. 11A illustrates that each tab member 77, 77' includes a respective semicircular recess 78, 78' at opposed ends thereof which cooperate to provide an access opening into the tube member passage 72. This collective access opening is diametrically sized to enable sliding insertion of the stent assembly 36 therethrough.

In accordance with the present invention, the retaining mechanism 76 preferably includes a pair of opposed sliding lock members 80, 80' which cooperate with the delivery apparatus to substantially prevent axial displacement of the stent assembly relative the tube member 69. Each lock member 80, 80' is slideably coupled to a respective tab member 77, 77' for movement between the released condition (FIG. 11B), out of frictional engagement with the delivery catheter, and the engaged condition (FIG. 11C), frictionally engaging the delivery catheter to prevent relative displacement between the tube member 69 and the stent assembly 36.

An elastomer seal 81, 81 ' is preferably included at the opposed ends of each lock member 80, 80' to form a fluid tight or hemostatic seal around the outer surface of the tube member 69 when the retaining mechanism is in the engaged condition. Accordingly, the elastomer seals 81, 81', in the engaged condition, cooperate to not only substantially prevent relative axial displacement of the stent delivery catheter apparatus 12, but also to form a fluid tight seal around the delivery catheter apparatus 12 at the proximal opening 73 to the receiving passage 72. Therefore, as best viewed in FIG. 11C, the opposed ends of elastomer seals 81, 81 ' must further engage one another in the engaged condition to form a fluid-tight seal with one another as well.

Each elastomer seal 81, 81' is preferably composed of a resilient material adapted to collectively conform to the transverse cross-sectional periphery of the delivery catheter apparatus 12. Once the opposed lock members 80, 80 are manually urged toward one another into engagement with the delivery catheter apparatus 12, the conformable elastomer seals seat up against the tube member peripheral surface. To facilitate fluid-tight conformance, each elastomer seal 81, 81' includes a semicircular hollow 82, 82' at the opposed ends therein. Thus, the diametric size of these recesses should be sized smaller than that of the delivery catheter to ensure sealing conformance therewith in the engaged condition. It will be appreciated, however, that such opposed hollows need not always be employed to conform about the delivery catheter.

In accordance with the present invention, each lock member 80, 80' is slideably coupled to the respective tab member 77, 77' through any conventional track assembly 83, 83' which enables relative linear displacement of the tab member 77, 77 toward the delivery catheter apparatus 12. Each track assembly 83, 83' includes a central slide member 85, 85' attached to the respective lock member 80, 80' to provided a sliding interface with the respective tab member 77, 77'. It will be appreciated, however, that any assembly enabling sliding movement may be employed.

Moreover, the retaining mechanism 76 is preferably configured to releasably affix the lock member 80, 80' in one of a plurality of positions between the released condition (FIG. 11B) and the engaged condition (FIG. 11C). This is especially important when the lock members are in the engaged condition so that the elastomer seals 81, 81' may be retained in fluid-tight contact with the delivery catheter apparatus 12. For example, the sliding lock member 80, 80' may be provided by a ratching mechanism which enables incremental locking movement. It will be appreciated, however, that other more conventional retaining mechanisms may be employed which eliminate or reduce relative axial displacement without departing from the true spirit and nature of the present invention.

In an alternative arrangement, the retaining mechanism 76 may be provided by an interference fit between the tube member 69 and the stent assembly. The wall 70 defining the receiving passage 72, for instance, may be sized to cause a slight interference fit with the stent assembly and/or the delivery catheter to substantially reduce or prevent inadvertent withdrawal or advancement of the same through the tube member 69. This interference, however, must not be so significant as to cause damage to the stent assembly during such axial displacement.

The tube member 69 is preferably composed of a material sufficiently flexible to resist lateral breakage or fracture during normal use and handling such as insertion into a Tuohy-Borst fitting. Moreover, as will be discussed, the material and design of the tube member 69 must be sufficiently crush resistance (in the range of about 0.1 lbs to about 20.0 lbs) to substantially maintain the inner diameter of the passage when a fluid seal is formed between the outer circumferential surface of the tube member and the fitting. This would allow the delivery catheter apparatus 12 to be axially displaced relative the tube member 69 during positioning and deployment of the stent assembly 36 in the vessel. A material having a durometer rating of between about 60 D to about 90 D, accordingly, is desirable. In one example, the tube member 69 is preferably composed of generally transparent polyurethane or polyether having a wall thickness of about 2 mils to about 40 mils, and more preferably about 4 mils to about 10 mils. Other suitable materials include polyvynols, resin based plastics, and woven composites, and even metal, as will be described in greater detail below.

During use of the shield assembly 30, the distal proboscis section 86 of the tube member 69 is dimensioned for sliding receipt in an access opening of a delivery fitting. As shown in FIGS. 12A–12C, to insert the stent assembly 36 into a vessel (not shown), the distal proboscis section 86 of the shield assembly 30 is preferably inserted into the Tuohy-Borst fitting 21 of a guiding catheter. Similar to the above embodiments, this union may be provided by a Y-adapter 22 having an adapter nut 23 tightened to the threaded end 24 to functionally couple and fluid seal the distal proboscis section 86 to the Y-adapter.

Subsequently, the retaining mechanism 76 may be moved to the released position (FIG. 11B) to enable relative axial displacement between the delivery catheter apparatus 12 and the tube member 69. The stent delivery catheter apparatus 12 and the delivery catheter apparatus 12 may the be forwardly advanced as a unit (FIG. 12B) into a passage 25 of the Y-adapter 22 and into the vessel. Accordingly, it will be appreciated that the distal proboscis section 86 must be sufficiently rigid and crush resistant to permit relative sliding displacement while simultaneously maintaining a fluid seal with the Tuohy-Borst fitting 21.

In accordance with the present invention, the tube member is preferably removed from supportive coupling to the delivery catheter apparatus 12 to facilitate maneuverability and deployment of the stent assembly 36. Thus, while the retaining mechanism 76 is maintained in the released position (FIG. 10B), the adapter nut 23 of the Tuohy-Borst fitting 21 may be loosened about the threaded end 24 to enable the distal proboscis section 86 of the tube member 69 to be withdrawn from delivery engagement with the Y-adapter (in the direction of arrow 87 in FIG. 12C). Once the distal proboscis section 86 is separated from the fitting 21, the adapter nut 23 may again be tightened to form a fluid seal with the delivery catheter apparatus 12. Subsequently, the removal structure 71 of the radiation shield assembly may be operated to enable separation of the tube member 69 from the delivery catheter.

Figure 13A:
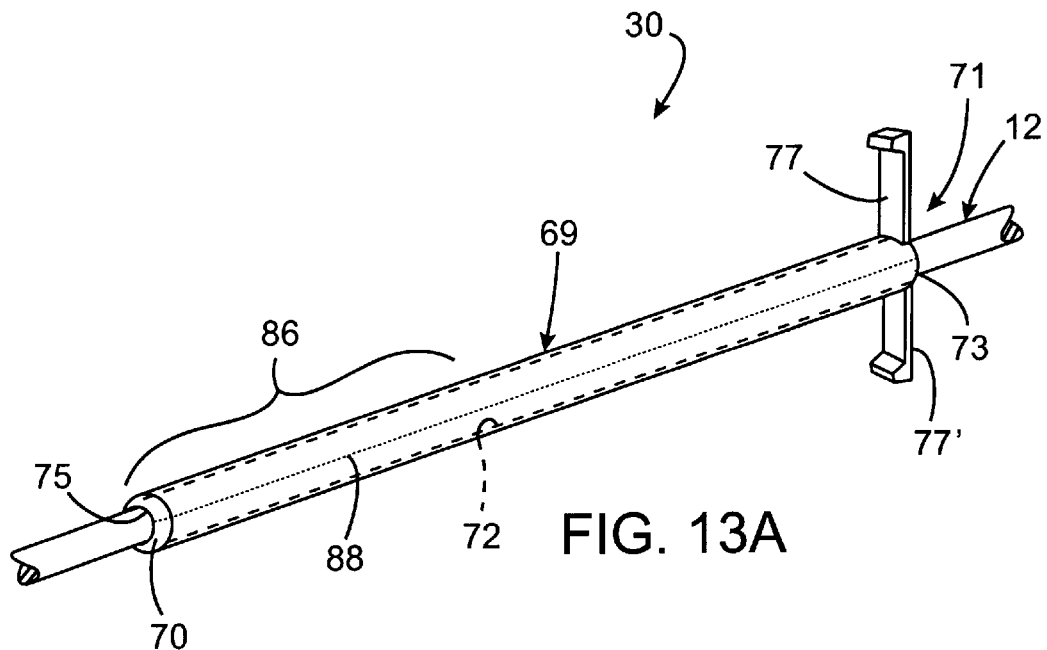
FIGS. 13A and 13B are a sequence of top perspective views of an alternative embodiment radiation shield assembly having a tube member with a pair of opposed tab members to facilitate removal from the delivery catheter.
Figure 13B:
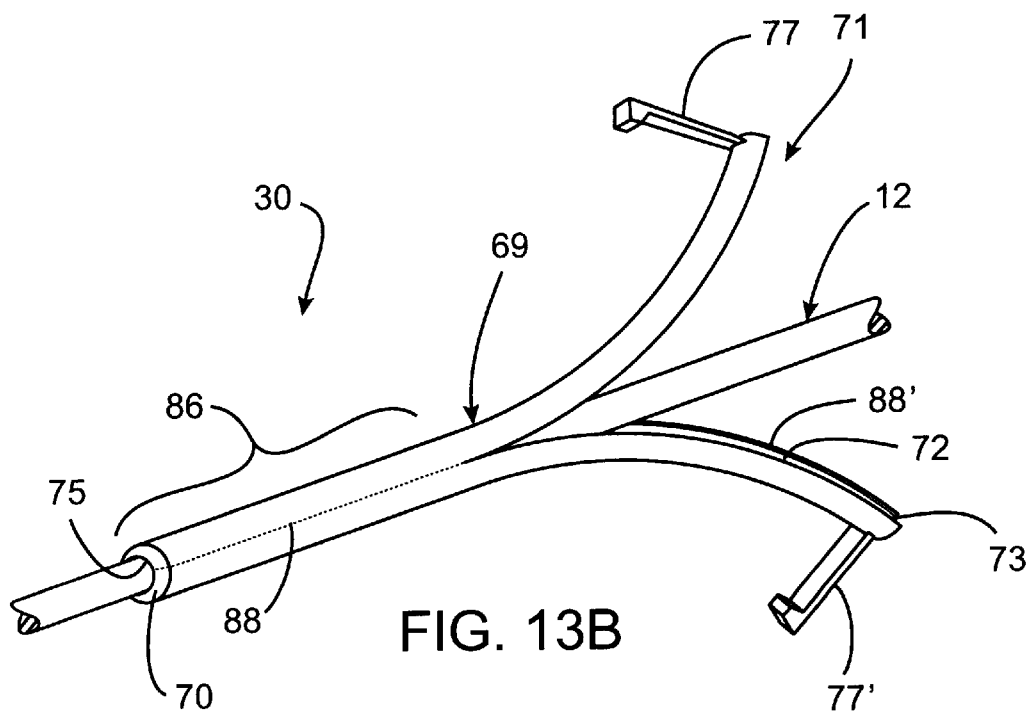

Referring now to FIGS. 10 and 13B, the removal structure 71 of the present invention selectively induces the tube member 69 to longitudinally split or sever open the receiving passage 72 so that delivery catheter apparatus 12 may be pulled-out of and separated from the passage 72. The tube member 69 is thus adapted to be torn (FIG. 10) or peeled-away (FIG. 13B) from the delivery catheter apparatus 12 in a manner longitudinally opening the receiving passage 72. Thus, the removal structure 71 may include a tab member 77 or the like protruding radially outward from the tube member 69. This tab member 77 is preferably integrally formed with the tube member and outwardly by a length sufficient to enable manual gripping thereof. By pulling the tab member 77 laterally away from the longitudinal axis of the delivery catheter apparatus 12. This causes the tube member to sever or split so that the tube member 69 can be removed from encumbered contact with the delivery catheter apparatus 12.

To facilitate longitudinal splitting or severing of the tube member, the removal structure 71 may further include a longitudinally extending perforation 88 or scoring, or the like. This perforation 88 preferably extends substantially linearly along one side of the tube member 69, and functions to slightly weaken the structure longitudinally therealong. Hence, when the tab member is urged away from the delivery catheter apparatus 12, the delivery catheter apparatus 12 in combination with the perforation 88 causes the tube member 69 to be torn or severed from the delivery catheter apparatus 12 as the same penetrates through the perforation 88 (FIG. 10). Accordingly, to further enhance the "peel" or "tear" away nature of this embodiment, the elongated perforation 88 is preferably longitudinally situated at a location opposite the tab member 77.

In another configuration (not shown), the removal structure may include a single continuous slit (similar to the continuous slit 90 in FIG. 14) extending longitudinally along the tube member 69 at a location opposite the tab member 77. To enclose the stent assembly 36, the opposed edges defining the continuous slit may be adhered together through a breakable bonding material or the like. Such a bonding material (similar to bonding material 95 in the embodiment of FIG. 14) applied between the edges of the slit must be sufficiently rigid to resist crushing when forming a fluid tight seal with the Touhy-Borst fitting 21, yet be breakable or capable of separation when the tab member is pulled and the delivery catheter is utilized to sever the bond. Typical of such bonding materials include liquid adhesives and biocompatible epoxies.

The tab member 77 of the removal structure 71 may further be provided by a rip cord or string member (not shown) embedded or cooperating with the tube member 69 for severing thereof. Hence, when the cord member is pulled, the tube member 69 is caused to tear longitudinally therealong in a manner permitting the tube member to be removed from the delivery catheter apparatus 12.

As best shown in FIGS. 13A and 13B, an alternative configuration of the removal structure 71 provides two opposed tab member 77, 77' both mounted to or integral with the tube member 69 and extending radially outward from the tube member 69 to enable gripping thereof. In this arrangement, the tab members 77, 77' maybe simultaneously gripped and pulled in opposite directions away from the longitudinal axis of the delivery catheter apparatus 12. This motion causes the tube member 69 to sever or split at two locations longitudinally along the tube member 69 which splits the same into two independent halves. During separation, the two halves may be essentially peeled-away and removed from the delivery catheter apparatus 12.

As mentioned above, these tab members 77, 77' may further be employed to form the support base for a respective sliding lock member 80, 80' of the retaining device. Thus, the tab members 77, 77' may have dual function capacity.

Similar to the pervious embodiment, this configuration may include a pair of opposed, longitudinally extending perforations or scoring marks 88, 88' to facilitate severing when the tab members 77, 77' are pulled in opposite directions. Each perforation 88, 88', therefore, is preferably positioned between the tab members 77, 77'.

In still another alternative embodiment to the removal structure 71, two independent longitudinally extending slits 90, 90' (FIGS. 14 and 15) may be provided which extend continuously from the proximal opening 73 to the distal opening 75. These slits 90, 90' are preferably oriented opposite one another, and extend longitudinally along the tube member 69. Accordingly, the tube member 69 includes two opposed tube sections 91, 91' which cooperate to enclose the stent assembly 36 when the sections are aligned in a closed condition (Similar to FIG. 12A and FIG. 14).

To mount or couple the two opposed tube sections 91, 91' together, a breakable heat seal (i.e., thermal bonding) or bond material 95, 95' is applied between the edges of the slits 90, 90'. These bond materials include EVA, PVA, or other elastomers, which provide a sufficiently rigid bond to resist crushing when forming a fluid tight seal with the Touhy-Borst fitting 21. Again, these bonds 95, 95' must be breakable or capable of separation when an appropriate degree of separation forces are applied to the adhered joints. Thus, the bonding strength must not be so great as to preclude manual separation, but not be so small as to sever when the compression forces of the Toiihy-Borst fitting 21 are applied.

Figure 15:
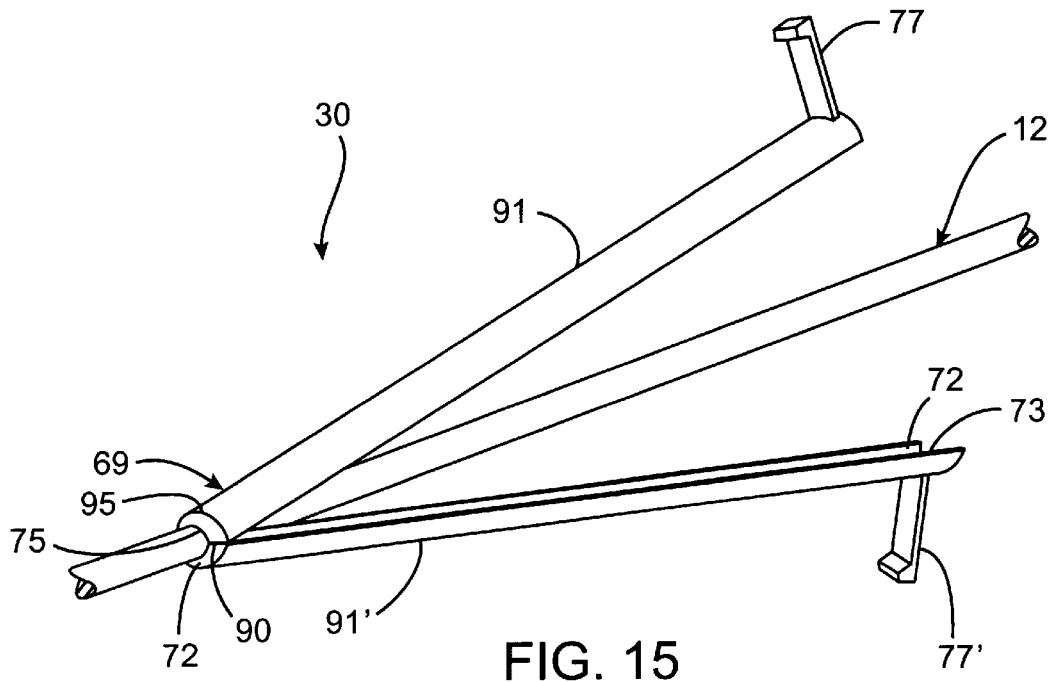
FIG. 15 is a fragmentary top perspective view of the tube member embodiment of FIG. 14 being separated for removal of the delivery catheter assembly.

Moreover, in this arrangement, the tube member 69 is preferably substantially rigid in nature, and is not "peeled" or "torn" away from the delivery catheter apparatus 12 in the same manner as with the more flexible tube members. Rather, the rigid nature promotes bonding, yet is more easily separable when the appropriate separation forces are applied (FIG. 15). In one example these opposed tube sections 91, 91', in this relatively rigid configuration, may even be composed of a metallic material.

Figure 14:
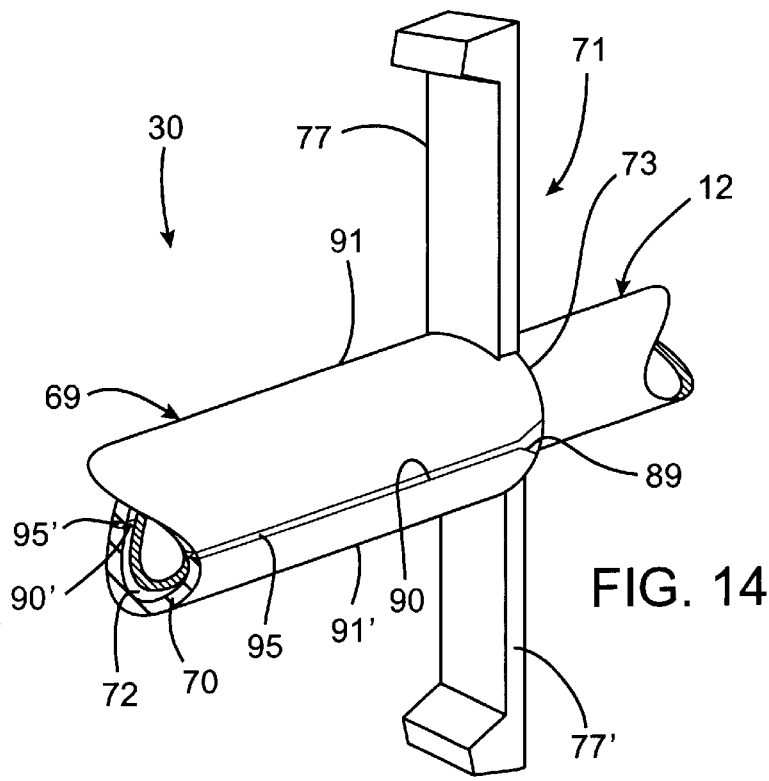
FIG. 14 is an enlarged, fragmentary, top perspective view of an alternative embodiment of the tube member of FIG. 13A and 11B composed of two opposed, substantially rigid tube sections coupled together through a separable bonding material.

To facilitate separation between the two halves, as shown in FIG. 14, the slits 90, 90' taper outwardly to form a notch 89 on each side of the proximal opening 73. This arrangement decreases the amount of force necessary break-away the tube. It will be appreciated that this concept is applicable to the other embodiments as well to facilitate the tear or peel-away of the tube.

While the elongated tube member 69 provides some degree of shielding when radioactive stents are being deployed, additional shielding may be desirable and even necessary. Accordingly, this embodiment of the radiation shield assembly 30 may further include a radiation shield device 92 (as illustrated in an opened position in FIG. 16) which cooperates with the elongated tube member 69 to further shield personnel from the radiation emitted from a radioactive stent. Similar to application of radiation shield embodiments of FIGS. 1–8, this shield device 92 is preferably provided by a two piece embodiment capable of selective removal from the delivery catheter to facilitate maneuverability thereof during stent positioning and deployment.

To provide the appropriate protective shielding, the stent assembly 36 contained in the tube member must be centrally located in the shield device 92. Thus, the channel 37 extending through the shield device 92 is formed and dimensioned for axial receipt of the tube member 69 therein, as shown in the opened position of FIG. 16. When the shield device 92 is moved to the closed position, similar to FIG. 2B for example, the two shield members 31, 33 cooperate to contain the tube member 69 and the stent delivery catheter apparatus 12 therein as a unit. Moreover the first mating surface 32 of the first shield member 31, and the opposed second mating surface 35 of the second shield member 33 cooperate to substantially radially enclose the stent 11 therebetween in a manner substantially preventing the direct passage of radioisotopes emitted from the stent radially out of the shield assembly 30.

In the preferred embodiment, the tube member 69 is slideably received in the channel 37 for relative axial displacement therebetween. To anchor the tube member 69 and the stent assembly 36 centrally in the radiation shield device 92, a Tuohy-Borst or similar fitting (not shown) may be included at the proximal end of the radiation shield device 92, and in communication with channel 37. By tightening an adapter nut of the fitting, the tube member may be prevented from axial displacement relative the shield device.

In the preferred embodiment and as shown in FIG. 16, however, the shield members 31, 33 each include respective slots 93, 93' which cooperate, when in the closed position, to receive the tab members 77, 77' therein. These receiving slots 93, 93' are preferably formed for an interference fit of the respective tab member 77, 77' therein to prevent axial displacement relative the shield device 92. Upon movement of the radiation shield device 92 to the opened position (FIG. 16), the tube member 69 together with the tab members 77, 77' of the retaining mechanism 71 may be removed from the channel 37 of the shield device.

Alternatively, the receiving slots 93, 93' may be positioned in an orientation (not shown) such that the tab members extend transverse to, as opposed to parallel with, the first mating surface 32 and the opposed second mating surface 35, when in the closed position. Accordingly, in this embodiment, when the first shield member 31 and the second shield member 33 are moved to the opened condition, the interference fit between the tab members 77, 77' and the respective receiving slots 93, 93' cause the tube member 69 to sever the wall 70 for removal of the delivery catheter 12. It will be understood that these receiving slot arrangements also apply to tube members with single tab members (i.e., FIGS. 9–12), as well.

FIG. 16 further illustrates that the tube member 69 is preferably substantially longer than the radiation shield device 92. The distal proboscis section 86 of the tube member 69 extends distally beyond the distal end of the shield device 92 to essentially form the proboscis 86 thereof. Accordingly, when the tube member 69 and the stent assembly 36 are retained in the shield device, the shield assembly 30 functions in a very similar manner as the shield assembly embodiment of FIG. 3.

Once the distal proboscis portion of the shield assembly 30 (i.e., of the tube member 69) is inserted into the Tuohy-Borst fitting 21 of the Y-adapter to form a fluid seal therewith (via adapter nut 23), the adapter nut of the shield device fitting 43 may be loosened while the retaining mechanism 76 is moved to the released position. Subsequently, the stent assembly 36 may be forwardly advanced into the Y-adapter, similar to FIG. 12B. The two-piece shield assembly may then be moved to the opened condition (FIG. 16) for removal from the tube member 69, and the tube member 69 may then be withdrawn from the Tuohy-Borst fitting 21 and separated from the delivery catheter apparatus 12 as above-discussed.

It will be appreciated that the single radiation shield device, such as that disclosed in U.S. Pat. No. 5,605,530, may be used in combination with tube member 69 without departing from the true spirit and nature of the present invention.

In another aspect of the present invention, a method is provided for storing a deformable stent 11 mounted onto a deployment portion 20 of a delivery apparatus 12 for transport and delivery of the stent 11. The method includes containing the stent 11 and the deployment portion 20 into an axially extending receiving passage 72 of a relatively thin, elongated tube member 69 to substantially prevent direct contact with the stent 11. In accordance with the present invention, the method further includes providing removal structure 71 cooperating with a wall 70 of the tube member 69 for longitudinal severing thereof to enable selective removal of the delivery apparatus 12 from the tube member 69 for deployment use thereof.

Another method is provided, as shown in FIGS. 9, 10 and 12A–12C, for delivering a deformable radioactive stent 11 mounted onto a deployment portion 20 of a delivery apparatus 12 which includes containing the stent 11 and the deployment portion 20 in a passage 72 of an elongated tube member 69 to substantially prevent direct contact with the stent 11 (FIG. 9); and placing a proboscis section 86 of the tube member 69 in communication with a fitting 21 (FIG. 12A) for receipt into the vessel. This aspect of the present invention further includes axially advancing the mounted stent 11 and the deployment portion 20, relative the tube member 69, into the fitting 21 (FIG. 12B); and removing the tube member 69 from impeding contact with the delivery apparatus 12 (FIGS. 10, 13B or 15).

In one embodiment, the placing a proboscis section 86 includes slideably inserting the proboscis section 86 into an opening of the fitting 21 to enable sliding axial receipt of the stent 11 and deployment portion 20 therein. As best viewed in FIG. 12C, prior to the removing the tube member event, the method includes withdrawing the proboscis section 86 of the tube member 69 from communication with the fitting 21.

Referring back to FIGS. 10, 13B and 15, the removing the tube member 69 includes the event of longitudinal severing the wall 70 of the tube member 69 to enable the selective removal of the delivery apparatus 12 from the tube member passage 72. This may be performed by tearing or peeling away the wall 70 of the tube member 69, or by breaking the bonding material 95 which may be applied to retain the tube member 69 in the closed position.

In the arrangement of FIGS. 12A–12C, the severing the wall 70 includes pulling a tab member 77 integrally formed in the wall 70 of the tube member 69. To facilitate separation of the delivery apparatus from the tube member during the severing motion, the method of the present invention further includes severing the wall 70 along a longitudinally extending perforation 88 predisposed in the wall 70. It will be appreciated that this method concept further applies to the embodiments which include opposed tab member arrangements, such as those of FIGS. 11–15.

Preferably, the containing the stent and deployment device further includes containing at least a portion of the elongated tube member in a radiation shield device 92 (FIG. 16) removably disposed peripherally about tube member 69 such that the stent 11 and the deployment portion 20 are substantially contained within the shield device 92. This containment substantially prevents the passage of radioisotopes emitted from the stent 11 radially out of the shield device 92. Accordingly, before the tube member 69 may be removed from the delivery apparatus 12, the radiation shield device must be removed from supportive contact with the delivery apparatus. This enables access to the tube member for severing of the tube member wall.

In the event the stent deployment is aborted while the catheter is received in the patient, the undeployed stent and the delivery device may be retracted back into the radiation shield without the inner-tube.

In another embodiment, the containing the stent and deployment device event further includes locking the delivery apparatus 12 to the tube member 69, through a retaining mechanism 76 (FIGS. 11A–11C), to substantially prevent axial displacement of the stent assembly 36 contained in the tube member passage 72. Moreover, before the axially advancing the stent assembly, the method preferably includes disengaging the retaining mechanism 76 (FIG. 11B) to permit axial displacement of the mounted stent 11 and deployment portion 20 relative the tube member passage 72.

As can be appreciated from the foregoing, the invention, in its various embodiments achieves the purpose of enclosing the stent and catheter assembly in an manner substantially preventing the direct passage of radioisotopes emitted from the stent radially out of the radiation shield assembly. At the same time, the present invention addresses the problems encountered in usage of the prior art invention such as inflexible usage and maneuverability by allowing the shield assembly to be taken apart at some point during or after the stent insertion procedure.

While this invention has been described in terms of several preferred embodiments, there are alterations, permutations, and equivalents which fall within the scope of this invention. For example, the two shield members may be movably coupled by any coupling device other than a hinge, a pin member or shrink wrap material, and each shield member may be made of more than one layer. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. A radiation shield assembly for a deformable stent mounted onto a deployment portion of a delivery apparatus comprising:

an elongated tube member defining a receiving passage formed and dimensioned for axial receipt of the stent mounted onto the deployment portion of the delivery apparatus therein to substantially prevent exposure to radiation of the stent, said tube member having a relatively thin wall portion, relative the length thereof, extending longitudinally from substantially one end of the tube member to an opposite end thereof; and removal structure cooperating with the thin wall portion of the tube member for longitudinal severing of the thin wall portion substantially from the one end of the tube member to the opposite end thereof to enable selective removal of the tube member from the delivery apparatus for deployment use thereof.

2. The radiation shield assembly according to claim 1 wherein, said tube member is deformable and adapted to peeled-away from the delivery apparatus upon severing of the wall portion.

3. The radiation shield assembly according to claim 1 wherein, said tube member is deformable and adapted to be torn away from the delivery apparatus upon severing of the wall portion.

4. The radiation shield assembly according to claim 1, wherein said tube member is formed for an interference fit with one of the mounted stent and the deployment portion of the delivery apparatus.

5. The radiation shield assembly according to claim 1 wherein, said tube member is composed of a flexible polymer material having a wall thickness in the range of about 2.0 Mils to about 40 Mils.

6. The radiation shield assembly according to claim 3 wherein, said removal structure includes a tab member coupled to said tube member to enable gripping thereof for said severing of the tube member wall portion.

7. The radiation shield assembly according to claim 6 wherein, said removal structure further includes a longitudinally extending perforation to facilitate separation of the delivery apparatus from the tube member during the severing motion.

8. The radiation shield assembly according to claim 1 wherein, said removal structure includes a longitudinally extending perforation to facilitate severing of the tube member wall during removal of the delivery apparatus from the tube member.

9. The radiation shield assembly according to claim 1 wherein, said removal structure includes a pair of opposed tab members coupled to said tube member to enable opposed gripping thereof for said severing of the tube member wall portion.

10. The radiation shield assembly according to claim 9 wherein, said removal structure further includes a pair of opposed longitudinally extending perforations each respectively positioned between said tab members to facilitate separation of the tube member from the stent during the removal thereof.

11. The radiation shield assembly according to claim 1 wherein, said tube member includes a relatively rigid first tube section, and an opposed relatively rigid second tube section which together cooperate, in a closed condition, to define the receiving passage for receipt of said stent and said deployment portion therein, and said removal structure including a bonding material cooperating with the first and second tube sections to retain said tube member in the closed condition, said bonding material further adapted to enable separation of the opposed first and second tube sections, to an opened condition, upon application of sufficient separation forces to overcome the bonding strength of the bonding material to sever said wall portion.

12. The radiation shield assembly according to claim 11 wherein, each said first tube section and said second tube section includes longitudinally extending first edge and an opposite longitudinally extending second edge wherein, in the closed condition, the respective first edges and the respect second edges are positioned adjacent one another, and said bonding material is disposed respectively therebetween for bonding thereof.

13. The radiation shield assembly according to claim 12 wherein, said first and second tube sections are comprised of metal.

14. The radiation shield assembly according to claim 1 further including:

a retaining mechanism coupled to said tube member and adapted to selectively prevent axial displacement between the deployment portion of the delivery apparatus and the tube member.

15. The radiation shield assembly according to claim 14 wherein, said retaining mechanism is movable between an engaged condition, preventing axial displacement between the stent and deployment portion of the delivery apparatus contained in the tube member passage, and a disengaged condition, permitting axial displacement therebetween.

16. The radiation shield assembly according to claim 15 wherein, said retaining mechanism includes a pair of opposed engaging fingers configured to contact the delivery apparatus for frictional engagement therewith in the engaged condition.

17. The radiation shield assembly according to claim 16 wherein, each engaging finger includes a seal member configured to cooperate with one another to form a hemostatic seal with said delivery apparatus when positioned in the engaged condition to seal the proximal end of said passage.

18. The radiation shield assembly according to claim 17 wherein, each seal member is provided by an elastomeric seal positioned at opposing distal ends of the respective engaging fingers.

19. The radiation shield assembly according to claim 16 wherein, each engaging finger is movably mounted to the tube member between the engaged condition and the disengaged condition in directions toward and away from the delivery apparatus.

20. The radiation shield assembly according to claim 19 wherein, said retaining mechanism further includes a lock device coupled to the engaging fingers for selective locking thereof in the engaged condition.

21. The radiation shield assembly according to claim 14 wherein, said retaining mechanism is positioned proximate a proximal section of said tube member, and includes a seal device adapted to form a hemostatic seal with said delivery apparatus when in the engaged condition to seal the proximal end of said passage.

22. The radiation shield assembly according to claim 9 further including:

a retaining mechanism coupled to the opposed tab members and adapted to selectively prevent axial displacement between the deployment device and the tube member.

23. The radiation shield assembly according to claim 22 wherein, said retaining mechanism is movable between an engaged condition, preventing axial displacement between the stent and deployment device contained in the tube member passage, and a disengaged condition, permitting axial displacement therebetween.

24. The radiation shield assembly according to claim 23 wherein, said retaining mechanism includes a pair of opposed engaging fingers each coupled to a respective tab member, and configured to contact the delivery apparatus for frictional engagement therewith in the engaged condition.

25. The radiation shield assembly according to claim 24 wherein, each engaging finger includes a seal member configured to cooperate with one another to form a hemostatic seal with said delivery apparatus when positioned in the engaged condition to seal the proximal end of said passage.

26. The radiation shield assembly according to claim 24 wherein, each engaging finger is movably mounted to the respective tab member between the engaged condition and the disengaged condition in directions toward and away from the delivery apparatus.

27. The radiation shield assembly according to claim 26 wherein, said retaining mechanism further includes a lock device coupled to the engaging fingers for selective locking thereof in the engaged condition.

28. A radiation shield assembly for a deformable radioactive stent mounted onto a deployment portion of a delivery apparatus comprising:

an elongated tube member having a wall defining a receiving passage formed and dimensioned for axial receipt of the stent mounted onto the deployment portion of the delivery apparatus therein; and radiation shield device removably disposed peripherally about at least a portion of said elongated tube member such that said stent and said deployment portion are substantially contained within said shield device to substantially prevent the passage of radioisotopes emitted from the stent radially out of said shield device.

29. The radiation shield assembly according to claim 28 wherein, said tube member includes removal structure cooperating with the wall of the tube member for longitudinal severing thereof to enable selective removal of the tube member from the delivery apparatus for deployment use thereof.

30. The radiation shield assembly according to claim 29 wherein, said tube member is adapted to peeled-away from the delivery apparatus upon severing of the wall.

31. The radiation shield assembly according to claim 29 wherein, said tube member is adapted to be torn away from the delivery apparatus upon severing of the wall.

32. The radiation shield assembly according to claim 31 wherein, said removal structure includes a tab member coupled to said tube member to enable gripping thereof for said severing of the tube member wall.

33. The radiation shield assembly according to claim 32 wherein, said removal structure further includes a longitudinally extending perforation to facilitate separation of the delivery apparatus from the tube member during the severing motion.

34. The radiation shield assembly according to claim 31 wherein, said tube member is sufficiently radially rigid to substantially withstand radial compressive forces in the range of about 0.1 to about 20 lbs.

35. The radiation shield assembly according to claim 34 wherein, said tube member is composed of a flexible polymer material having a wall thickness in the range of about 2.0 mils inch to about 40.0 mils.

36. The radiation shield assembly according to claim 31 wherein, said tube member includes a distal proboscis portion adapted to extend distally from said radiation shield when said stent is contained therein.

37. The radiation shield assembly according to claim 36 wherein, said tab member is positioned on a proximal section of the tube member.

38. The radiation shield assembly according to claim 28 wherein,
said radiation shield device is configured to enable said delivery apparatus and the mounted tube member to be axially displaceable therewith.

39. The radiation shield assembly according to claim 28 wherein,
said radiation device includes a first shield member having a first mating surface, and a second shield member removably coupled to said first shield member, and having an opposed second mating surface cooperating with said first mating surface to substantially radially enclose the tube member and contained stent therebetween.

40. The radiation shield assembly according to claim 39 wherein,
said first mating surface and said second mating surface further cooperate to define a channel therebetween, formed and dimensioned for longitudinal receipt of the tube member therein.

41. The radiation shield assembly according to claim 40 further including:
a coupling device movably coupling said second shield member to the first shield member between a closed position, enclosing at least said tube member and the stent in said channel, and an opened position, enabling removal of said tube member from said shield device.

42. The radiation shield assembly according to claim 40 wherein,
said tube member includes a distal proboscis portion adapted to extend distally from said channel of the radiation shield when said stent is contained therein.

43. The radiation shield assembly according to claim 42 wherein,
said tube member includes removal structure adapted to enable removal of the tube member from the delivery apparatus.

44. The radiation shield assembly according to claim 43, wherein
said tube member is adapted to be torn away from the delivery apparatus upon severing of the wall.

45. The radiation shield assembly according to claim 44 wherein,
said removal structure includes a tab member coupled to said tube member to enable gripping thereof for said severing of the tube member wall.

46. The radiation shield assembly according to claim 45 wherein,
said removal structure further includes a longitudinally extending perforation to facilitate separation of the delivery apparatus from the tube member during the severing motion.

47. The radiation shield assembly according to claim 28 further including:
a retaining mechanism coupled to said tube member and adapted to selective prevent axial displacement between the deployment device and the tube member.

48. The radiation shield assembly according to claim 47 wherein,
said retaining mechanism is movable between an engaged condition, preventing axial displacement between the stent and deployment device contained in the tube member passage, and a disengaged condition, permitting axial displacement therebetween.

49. A method of storing a deformable stent mounted onto a deployment portion of a delivery apparatus for transport and delivery comprising:
containing the stent and the deployment device into an axially extending receiving passage of a relatively thin, elongated tube member to substantially prevent direct contact with the stent; and
providing removal structure cooperating with a wall of the tube member for longitudinal severing thereof to enable selective removal of the delivery apparatus from the tube member for deployment use thereof.

50. A method of delivering a deformable radioactive stent mounted onto a deployment portion of a delivery apparatus into a vessel comprising:
containing the stent and the deployment device in a passage of an elongated tube member to substantially prevent direct contact with the stent;
placing a proboscis portion of the tube member in communication with a fitting for receipt into the vessel;
axially advancing the mounted stent and the deployment device, relative the tube member, into the fitting; and
removing the tube member from impeding contact with the delivery apparatus.

51. The method of claim 50 wherein,
said placing a proboscis portion includes slideably inserting the proboscis portion into an opening of the fitting to enable sliding axial receipt of the stent and deployment portion therein.

52. The method of claim 50 wherein,
before the removing the tube member, withdrawing the proboscis portion of the tube member from communication with the fitting.

53. The method of claim 50 wherein,
said removing the tube member includes longitudinal severing a wall of the tube member to enable the selective removal of the delivery apparatus from the tube member passage.

54. The method of claim 53 wherein,
said longitudinal severing includes tearing-away the wall of the tube member to enable the selective removal of the delivery apparatus from the tube member passage.

55. The method of claim 54 wherein,
said severing a wall includes pulling a tab member integrally formed in the wall of the tube member to enable severing of the tube member wall.

56. The method of claim 54 wherein,
said severing a wall further includes severing the wall along a longitudinally extending perforation predisposed in the wall to facilitate separation of the delivery apparatus from the tube member during the severing motion.

57. The method of claim 50 wherein,
the containing the stent and deployment device further includes containing at least a portion of said elongated tube member in a radiation shield device removably disposed peripherally about tube member such that said stent and said deployment portion are substantially contained within said shield device to substantially prevent the passage of radioisotopes emitted from the stent radially out of said shield device.

58. The method of claim 57 wherein,
before the removing the tube member, removing the radiation shield device from contact with the delivery apparatus.

59. The method of claim 57 wherein,
said radiation shield device includes a first shield member having a first mating surface, and a second shield member an opposed second mating surface, said second shield member be movably coupled to said first shield member between a closed condition, substantially radially enclosing at least a portion of the tube member and the contained stent therebetween, and an opened condition, enabling removal of the tube member from the shield device, and said removing the radiation shield device includes moving the shield device from the closed condition to the opened condition.

60. The method of claim 59 wherein, said removing the tube member includes longitudinal severing a wall of the tube member to enable the selective removal of the delivery apparatus from the tube member passage.

61. The method of claim 50 wherein, the containing the stent and deployment device further includes locking the delivery apparatus to the tube member, through a retaining mechanism, to substantially prevent axial displacement of the mounted stent and deployment device contained in the tube member passage; and before the axially advancing the mounted stent and the deployment device, disengaging the retaining mechanism to permit axial displacement of the mounted stent and deployment device relative the tube member passage.

62. A shield assembly for a deformable stent mounted onto a deployment portion of a delivery apparatus comprising:

a relatively thin, elongated tube member having a wall defining a receiving passage formed and dimensioned for axial receipt of the stent mounted onto the deployment portion of the delivery apparatus therein to substantially prevent direct contact with the stent;

removal structure cooperating with the wall of the tube member for longitudinal severing thereof to enable selective removal of the tube member from the delivery apparatus for deployment use thereof; and a retaining mechanism having a pair of opposed engaging fingers movable between an engaged condition, adapted to contact the delivery apparatus for frictional engagement therewith to prevent axial displacement of the stent and delivery apparatus relative the tube member, and a disengaged condition, permitting axial displacement therebetween.

63. The radiation shield assembly according to claim 62 wherein, said tube member is deformable and adapted to peeled-away from the delivery apparatus upon severing of the wall.

64. The radiation shield assembly according to claim 62 wherein, said tube member is deformnable and adapted to be torn away from the delivery apparatus upon severing of the wall.

65. The radiation shield assembly according to claim 62, wherein said tube member is formed for an interference fit with one of the mounted stent and the deployment portion of the delivery apparatus.

66. The radiation shield assembly according to claim 64 wherein, said removal structure includes a tab member coupled to said tube member to enable gripping thereof for said severing of the tube member wall.

67. A shield assembly for a deformable stent mounted onto a deployment portion of a delivery apparatus comprising:

a relatively thin, elongated tube member having a wall defining a receiving passage formed and dimensioned for axial receipt of the stent mounted onto the deployment portion of the delivery apparatus therein to substantially prevent direct contact with the stent;

removal structure cooperating with the wall of the tube member for longitudinal severing thereof to enable selective removal of the tube member from the delivery apparatus for deployment use thereof;

a retaining mechanism positioned proximate a proximal section of said tube member and coupled thereto to selectively prevent axial displacement between the deployment device and the tube member, said retaining device further including a seal device adapted to form a hemostatic seal with said delivery apparatus when in the engaged therewith to seal the proximal end of said passage.

68. The radiation shield assembly according to claim 67 wherein, said tube member is deformable and adapted to peeled-away from the delivery apparatus upon severing of the wall.

69. The radiation shield assembly according to claim 67 wherein, said tube member is deformable and adapted to be torn away from the delivery apparatus upon severing of the wall.

70. The radiation shield assembly according to claim 67, wherein said tube member is formed for an interference fit with one of the mounted stent and the deployment portion of the delivery apparatus.

71. The radiation shield assembly according to claim 69 wherein, said removal structure includes a tab member coupled to said tube member to enable gripping thereof for said severing of the tube member wall.

* * * * *